United States Patent
Li et al.

(10) Patent No.: US 11,918,951 B2
(45) Date of Patent: Mar. 5, 2024

(54) MOF COMPOSITIONS FOR SELECTIVE SEPARATION OF HYDROCARBONS

(71) Applicant: Rutgers, The State University of New Jersey, New Brunswick, NJ (US)

(72) Inventors: Jing Li, Piscataway, NJ (US); Hao Wang, Shenzhen (CN)

(73) Assignee: Rutgers, The State University of New Jersey, New Brunswick, NJ (US)

(*) Notice: Subject to any disclaimer, the term of this patent is extended or adjusted under 35 U.S.C. 154(b) by 423 days.

(21) Appl. No.: 17/274,388

(22) PCT Filed: Sep. 13, 2019

(86) PCT No.: PCT/US2019/051116
§ 371 (c)(1),
(2) Date: Mar. 8, 2021

(87) PCT Pub. No.: WO2020/060873
PCT Pub. Date: Mar. 26, 2020

(65) Prior Publication Data
US 2021/0339186 A1    Nov. 4, 2021

Related U.S. Application Data

(60) Provisional application No. 62/731,555, filed on Sep. 14, 2018.

(51) Int. Cl.
C07F 15/02    (2006.01)
B01D 53/04   (2006.01)
(Continued)

(52) U.S. Cl.
CPC .......... B01D 53/0423 (2013.01); C07F 5/003 (2013.01); C07F 7/003 (2013.01);
(Continued)

(58) Field of Classification Search
CPC ................ B01D 53/04; B01D 53/0423; B01D 2253/204; B01D 2256/24;
(Continued)

(56) References Cited

U.S. PATENT DOCUMENTS

2012/0091064 A1* 4/2012 Schubert ............... C07C 51/418
210/660
2012/0115961 A1* 5/2012 Hafizovic ............... C07C 63/15
556/51
(Continued)

FOREIGN PATENT DOCUMENTS

CN    109400891 A    3/2019
EP    2998378 A1    3/2016
WO   2015177511 A1   11/2015

OTHER PUBLICATIONS

Suh, et al., "Hydrogen Storage in Metal-Organic Frameworks", Chen Rev, vol. 112, 2012, pp. 782-835.
(Continued)

*Primary Examiner* — Frank M Lawrence, Jr.
(74) *Attorney, Agent, or Firm* — Saul Ewing LLP; Domingos J. Silva; Kevin T. O'Brien

(57) ABSTRACT

The present disclosure relates to novel metal-organic frameworks (MOFs) comprising tetratopic ligands with small pore apertures. The present disclosure further relates to methods of utilizing the MOFs of the disclosure to separate hydrocarbons through adsorptive processes.

20 Claims, 29 Drawing Sheets

(51) Int. Cl.
*C07F 5/00* (2006.01)
*C07F 7/00* (2006.01)
*C07F 15/04* (2006.01)

(52) U.S. Cl.
CPC .... *B01D 2253/204* (2013.01); *B01D 2256/24* (2013.01); *B01D 2257/7022* (2013.01)

(58) Field of Classification Search
CPC ............ B01D 2257/7022; B01J 20/226; C07F 5/003; C07F 7/003; C07F 7/13; C07F 9/08; C07F 11/06
USPC ........................ 96/108; 95/143, 144; 502/401
See application file for complete search history.

(56) References Cited

U.S. PATENT DOCUMENTS

| | | | |
|---|---|---|---|
| 2014/0284829 A1* | 9/2014 | Maspoch Comamala | ................... C07F 19/00 264/12 |
| 2017/0247622 A1 | 8/2017 | Eddaoudi et al. | |
| 2018/0264434 A1* | 9/2018 | Alezi | ................. B01D 53/0476 |
| 2019/0224643 A1* | 7/2019 | Belmabkhout | ......... C10L 3/103 |
| 2021/0395275 A1* | 12/2021 | Li | ............................. C07F 3/04 |

OTHER PUBLICATIONS

Wang, et al., "Metal-Organic Frameworks Based on Double-Bond-Coupled Di-Isophthalate Linkers with High Hydrogen and Methane Uptakes", Chem Mater, vol. 20, 2008, pp. 3145-3152.

Xue, et al., "Topology meets MOF chemistry for pore-aperture fine tuning: ftw-MOF platform for energy-efficient separations via adsorption kinetics or molecular sieving", Chem Commun, 2018, 54, 6404-6407.

Xue, et al., "Topology meets MOF chemistry for pore-aperture fine tuning: ftw-MOF platform for energy-efficient separations via adsorption kinetics or molecular sieving", Chem Commun, 2018, 54, 6404-6407 Supplementary Material S1-S27.

International Search Report & Written Opinion dated Mar. 9, 2020 for corresponding International Application PCT/US2019/051116.

Wang, et al., "Topologically guided tuning of Zr-MOF pore structures for highly selective separation of C6 alkane isomers", Nature Comm, vol. 9, No. 1, 2018, pp. 1745 (11 pgs).

EP Search Report dated May 3, 2022 for corresponding European Application 19 861 474.5.

* cited by examiner

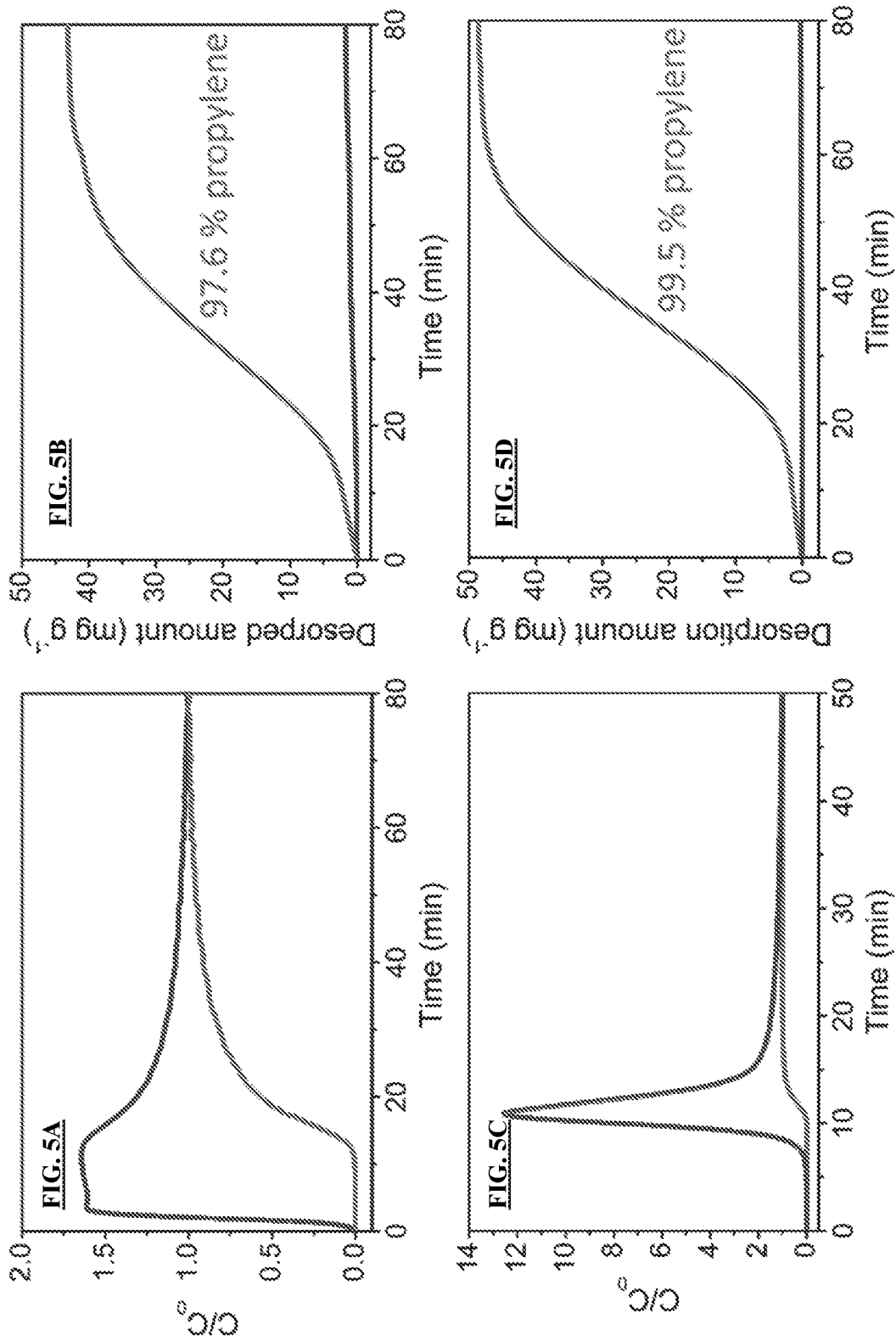

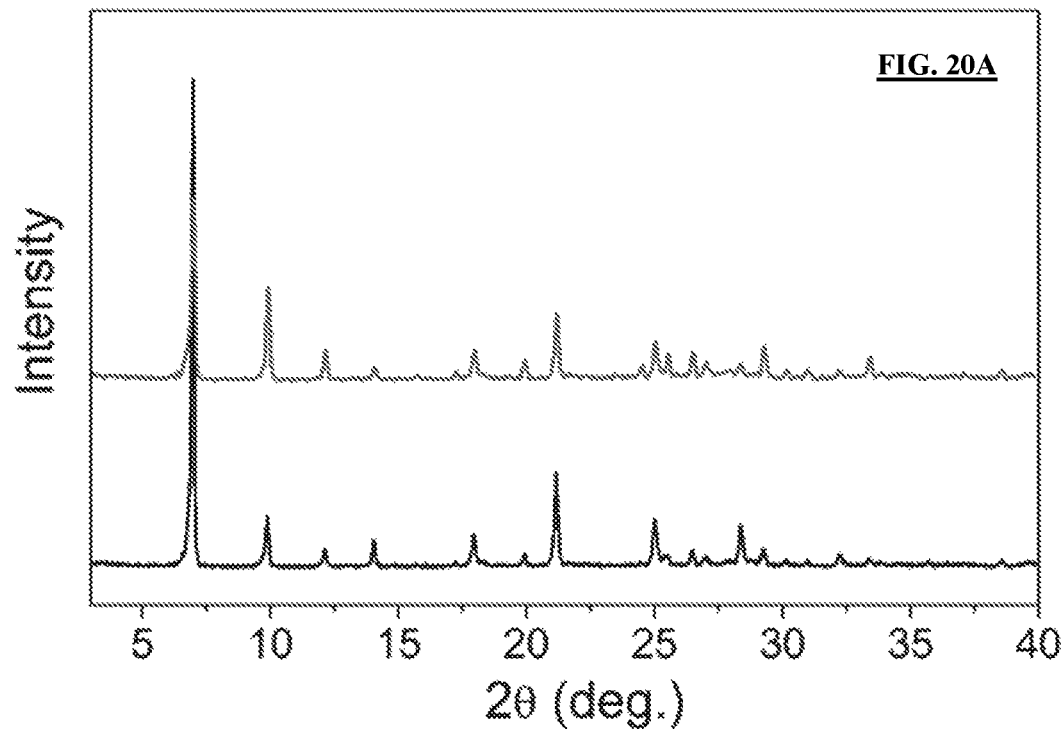
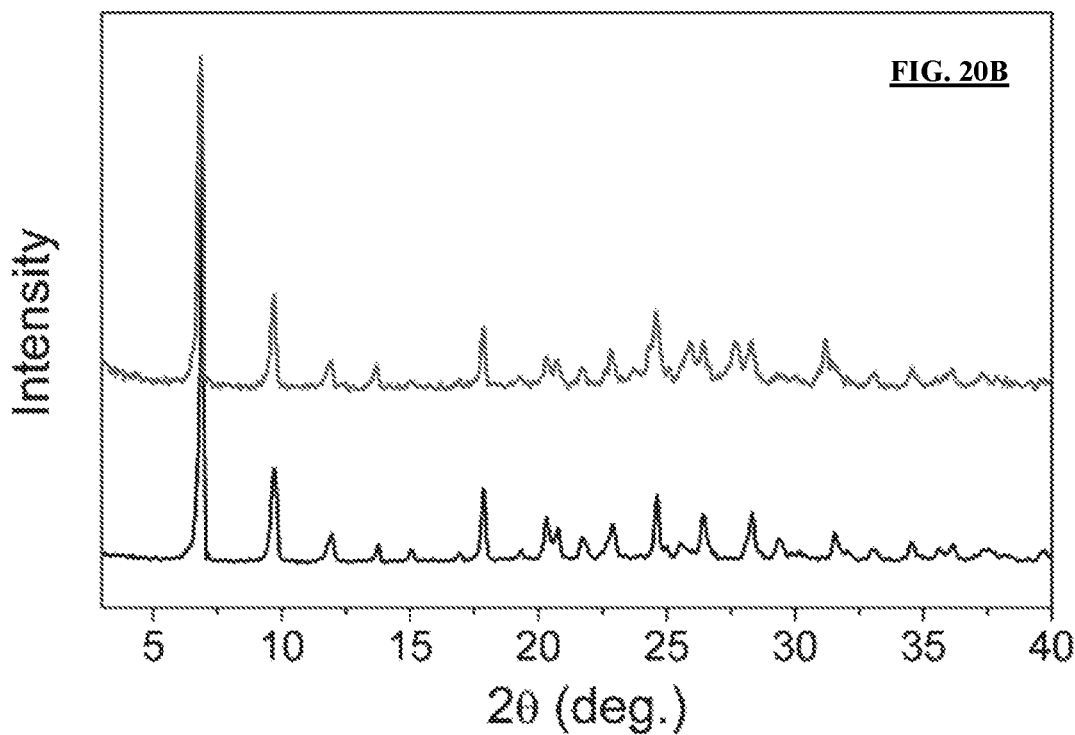

MOF COMPOSITIONS FOR SELECTIVE SEPARATION OF HYDROCARBONS

CROSS-REFERENCE TO RELATED APPLICATIONS

The present application is a 35 U.S.C. § 371 national phase application from, and claims priority to, PCT International Patent Application No. PCT/US2019/051116, filed Sep. 13, 2019, which claims priority under 35 U.S.C. § 119(e) to U.S. Provisional Application No. 62/731,555, filed Sep. 14, 2018, all of which is are hereby incorporated by reference herein in their entireties.

STATEMENT REGARDING FEDERALLY SPONSORED RESEARCH OR DEVELOPMENT

This invention was made with government support under DE-FG02-08ER-46491 awarded by Department of Energy. The government has certain rights in the invention.

BACKGROUND OF THE INVENTION

Paraffin/olefin separation, listed among the "seven chemical separations to change the world", is of high commercial importance, as highly pure olefins (e.g. propylene and ethylene) are required to comply with "polymer-grade" specifications for the manufacture of plastics. However, the separation is particularly difficult to accomplish because of the close volatilities of the components.

Propylene is one of the most important olefins in petrochemical industry, primarily because of its use in the production of polypropylene, the world's second-most widely produced synthetic plastic. The global demand for polypropylene has been rising continuously, and its annual growth rate is expected to be 4-5% before 2020, resulting in increasing need for polymer-grade (>99.5%) propylene. Nevertheless, the production of highly pure propylene represents a challenging and complicated process, which involves the separation of propylene from a propane/propylene mixture. Propane/propylene mixtures are typically obtained by steam cracking of naphtha or during fluid catalytic cracking of gas oils in refineries, with a propylene purity of 50-60% for the former and 80-87% for the latter. Conventional separation of propane and propylene relies on cryogenic distillation, which is carried out at about 243 K and 0.3 MPa in a column containing over 100 trays. This heat-driven process is highly energy-intensive.

To lower the energy and operational cost and to suppress the carbon emissions associated with the propylene purification process through cryogenic distillation, several alternative technologies have been proposed. Among them, adsorptive separation, such as pressure/temperature swing adsorption and gas phase simulated moving bed, can potentially offer higher energy efficiency. In this context, the development of a suitable adsorbent is of paramount importance for successful implementation of the adsorptive separation technology. To this end, a wide variety of porous solids have been examined for the separation of propane and propylene, including silica-gel, zeolites, and carbon molecular sieves to name a few. However, these materials have yet to meet the stringent requirement for industrial implementation, and thus, search for ideal adsorbents remains ongoing.

There remains a need in the art for methods and materials capable of separating hydrocarbon compounds efficiently and economically. In certain embodiments, such methods should allow for the separation of propylene from propane. The present invention meets this need.

BRIEF SUMMARY OF THE INVENTION

The invention provides a metal-organic framework comprising a certain metal (M) ion and a certain tetratopic organic ligand. In certain embodiments, the metal is Y. In other embodiments, the metal is Zr. In yet other embodiments, the metal is Hf. In yet other embodiments, the metal ion is $M^{3+}=Y^{3+}$. In yet other embodiments, the metal ion is $M^{4+}=Zr^{4+}$. In yet other embodiments, the metal ion is $M^{4+}=He^{+}$. In yet other embodiments, the tetratopic organic ligand is

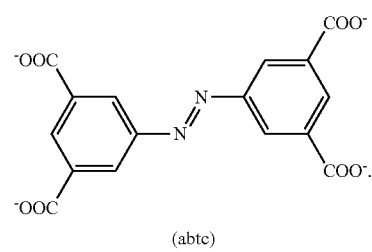

(abtc)

In other embodiments, the tetratopic organic ligand is

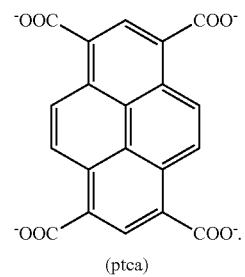

(ptca)

In yet other embodiments, the tetratopic organic ligand is

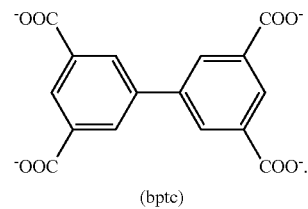

(bptc)

In yet other embodiments, the tetratopic organic ligand is

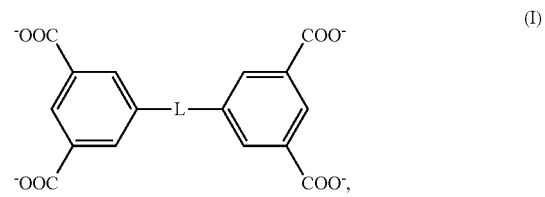

(I)

wherein L is selected from the group consisting of a bond, optionally substituted $C_1$-$C_6$ alkylene, optionally substituted $C_2$-$C_6$ alkenylene, optionally substituted $C_2$-$C_6$ alkynylene,

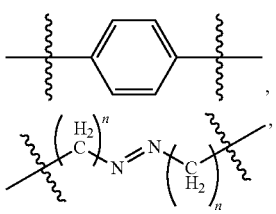

O, S, $SO_2$, NH and $NCH_3$; and each instance of n is independently an integer from 0 to 3.

The invention further provides a method of at least partially separating a first aliphatic hydrocarbon compound from at least one distinct aliphatic hydrocarbon compound. In certain embodiments, the method comprises contacting the first aliphatic hydrocarbon compound and the at least one distinct aliphatic hydrocarbon compound with a metal-organic framework contemplated in the invention. In other embodiments, the first aliphatic hydrocarbon compound and the at least one distinct aliphatic hydrocarbon compound are at least partially separated from one another.

BRIEF DESCRIPTION OF THE FIGURES

For the purpose of illustrating the invention, depicted in the drawings are certain embodiments of the invention. However, the invention is not limited to the precise arrangements and instrumentalities of the embodiments depicted in the drawings.

FIG. 4A shows a set of powder X-ray diffraction patterns and FIG. 4B shows propylene adsorption for "as synthesized" Y-abtc and after thermal and hydrothermal treatments.

FIGS. 5A-5D illustrate graphs showing multicomponent column breakthrough results for Y-abtc at 25° C. FIG. 5A is a breakthrough curve and FIG. 5B is a desorption curve for an equimolar mixture of propane and propylene. FIGS. 5C-5D are a breakthrough curve and desorption curve, respectively, for a mixture of propane/propylene with a feed ratio of 5/95. Color scheme: red: propylene, blue: propane.

(FIG. 6A) and the corresponding pore size distribution (FIG. 6B). (FIG. 6C) and the corresponding pore size distribution (FIG. 6D).

FIGS. 20A-20B illustrate PXRD patterns of Y-bptc (FIG. 20A) and Y-abtc (FIG. 20B) synthesized with small scale (lower line, starting with 38.3 mg $Y(NO_3)_3.6H_2O$) and 50× scaled up (upper line).

(FIG. 22A) and 300° C. (FIG. 22B). The activated MOF was digested in NaOD (1 mmol/L in $D_2O$).

DETAILED DESCRIPTION OF THE INVENTION

Figure 1A:
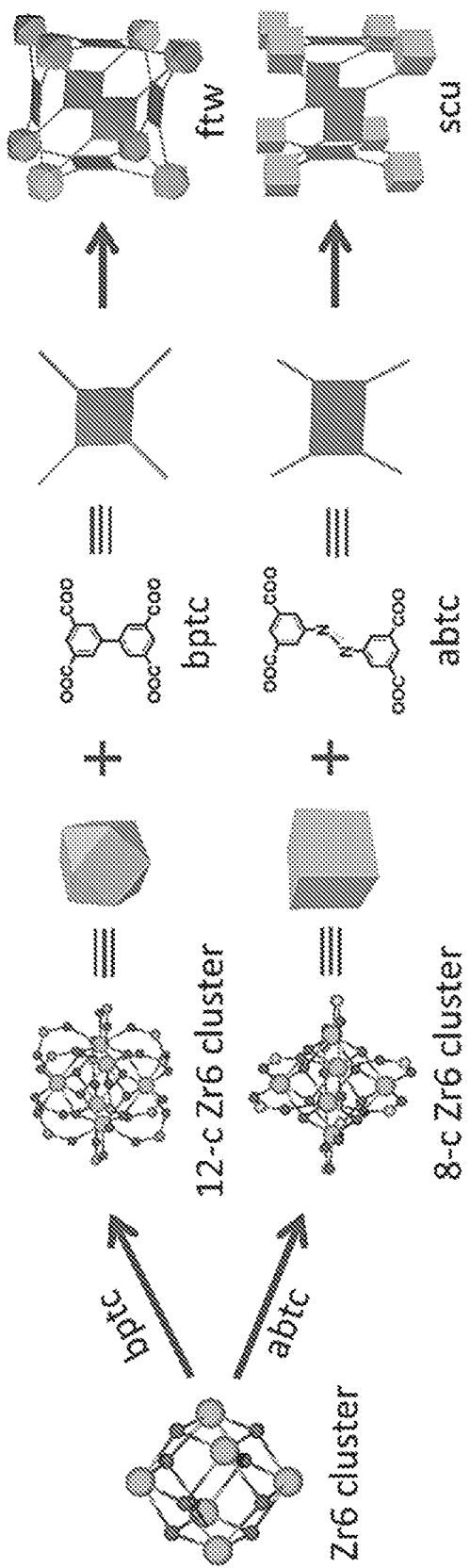
FIGS. 1A-1B illustrate a topology analysis of MOFs built on Zr6/Y6 clusters and two tetratopic ligands. Zr-bptc and Zr-abtc show different connectivity and topology due to the aspect ratio difference of the organic ligands. Y-bptc and Y-abtc feature similar connectivity and topology to that of Zr-bptc. Hydrogen atoms are omitted for clarity.

The present invention relates to the unexpected discovery of novel metal-organic frameworks (MOFs) comprising tetratopic ligands with pore apertures that allow for separation of hydrocarbons, such as propane/propylene. The present invention further relates to methods of utilizing the MOFs of the invention to separate hydrocarbons, including propylene, through adsorptive processes.

Disclosure

The newly emerged family of crystalline sorbent materials, metal-organic frameworks (MOFs), hold particular promise for hydrocarbon separation, including paraffin/olefin separation, in light of their tunable pore size, pore shape, and surface functionality. MOFs with open metal sites show favorable adsorption toward olefins over paraffins as a result of a side-on coordination of olefins at the unsaturated metal centers. Thus, this type of MOF materials, analogous to π-complexation zeolites/mesoporous silica, are capable of discriminating multiple olefins (e.g. ethylene+propylene) from paraffins through thermodynamically-driven separation.

On the other hand, in the case of propane/propylene separation, where the removal of a single olefin from its corresponding paraffin is needed, kinetically-driven separation often proves to be more suitable and efficient. A number of adsorbents have been reported to undergo kinetic separation toward propane and propylene. Compared to conventional adsorbents, the MOF pore size can be tuned much more readily to achieve significantly improved performance for kinetic separation of the two C3 molecules, as demonstrated in several recent studies. Yet another separation mechanism is based on selective size exclusion where one adsorbate is adsorbed while the other is completely excluded. This mechanism is considered an ideal scenario for gas separation as it offers the highest separation selectivity among three different mechanisms. A widely studied example is Zeolite 4A, as it selectively adsorbs propylene but excludes propane. However, its adsorption kinetics for propylene is very slow, resulting in poor separation performance under mixed-gas conditions.

In certain embodiments, the present invention includes a novel MOF family comprising structures built on a metal ion and tetratopic carboxylate ligands. In other embodiments, the metal is Y. In yet other embodiments, the metal is Zr. In yet other embodiments, the metal is Hf.

One embodiment of the invention includes two different organic ligands with similar geometry but different aspect ratios, 3,3',5,5'-biphenyltetracarboxylate (bptc; which corresponding acid is 3,3',5,5'-biphenyltetracarboxylic acid or H₄bptc), and (E)-5,5'-(diazene-1,2-diyl)diisophthalate (abtc; which corresponding acid is (E)-5,5'-(diazene-1,2-diyl)diisophthalic acid or H₄abtc).

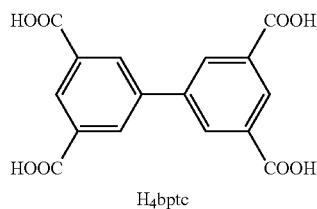

H₄bptc

-continued

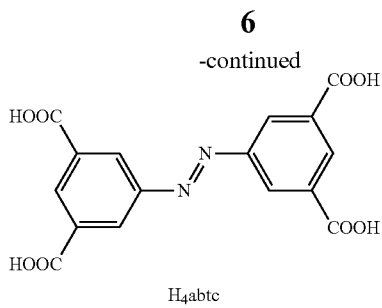

H₄abtc

Crystals were obtained for both Y-MOF compounds after optimization of synthetic conditions. Y-bptc and Y-abtc are highly stable frameworks with optimal pore structure for the separation of propylene and propane.

One embodiment of the invention includes the organic ligand pyrene-1,3,6,8-tetracarboxylate (ptca; which corresponding acid is pyrene-1,3,6,8-tetracarboxylic acid or H₄ptca):

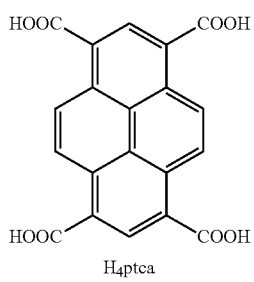 [SMILES: O=C(O)c1cc(C(=O)O)c2ccc3c(C(=O)O)cc(C(=O)O)c4ccc1c2c43]

H₄ptca

Crystals were obtained for the M-MOF (M=Zr, Hf, Y) compounds after optimization of synthetic conditions. M-ptca's are highly stable frameworks with optimal pore structure for the separation of propylene and propane.

Demonstrated herein are a family of microporous metal-organic framework materials with cage-like pores, that exhibit fast and complete separation of propane/propylene mixtures through a selective molecular exclusion mechanism. The optimal pore structure of this material was achieved by a topology-guided design strategy, involving the precise tuning of pore size by judicious selection of structure topology, inorganic nodes and organic ligands. Like zeolite 4A, the MOFs contemplated in the invention adsorb propylene but fully exclude propane, yet are superior to zeolite 4A as they exhibit much faster adsorption kinetics for propylene.

Multicomponent column breakthrough measurements demonstrated that the MOF contemplated in the invention is capable of producing propylene with a purity of 99.5% from a typical mixture concentration of cracking product, meeting the "polymer grade" specification required for the production of polypropylene. This structure, built on hexanuclear M₆ clusters, exhibits high thermal and hydrothermal stability. In addition, its synthesis is facile and can be easily scaled up.

Metal-Organic Frameworks

In one aspect, the invention provides a metal-organic framework comprising at least one $M^{3+}$ or $M^{4+}$ and $H_4ptca$:

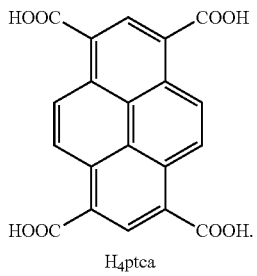 [SMILES: O=C(O)c1cc(C(=O)O)c2ccc3c(C(=O)O)cc(C(=O)O)c4ccc1c2c43]

$H_4ptca$

In one aspect, the invention provides a metal-organic framework comprising at least one $M^{3+}$, and at least one tetratopic organic ligand of formula (I):

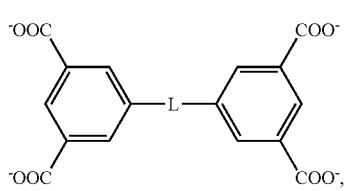

(I)

wherein:
L is selected from the group consisting of a bond, optionally substituted $C_1$-$C_6$ alkylene, optionally substituted $C_2$-$C_6$ alkenylene, optionally substituted $C_2$-$C_6$ alkynylene,

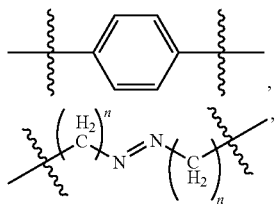

O, S, $SO_2$, NH and $NCH_3$; and
each instance of n is independently an integer from 0 to 3.

In certain embodiments, $M^{3+}$ is a metal selected from the group consisting of $Y^{3+}$, $Tb^{3+}$, $La^{3+}$, and $In^{3+}$. In other embodiments, $M^{3+}$ is $Y^{3+}$. In yet other embodiments, $M^{3+}$ is $Tb^{3+}$. In yet other embodiments, $M^{3+}$ is $La^{3+}$. In other embodiments, $M^{3+}$ is $In^{3+}$.

In certain embodiments, $M^{4+}$ is a metal selected from the group consisting of $Zr^{4+}$ and $Hf^{4+}$. In other embodiments, $M^{4+}$ is $Zr^{4+}$. In other embodiments, $M^{4+}$ is $Hf^{4+}$.

In certain embodiments, the $M^{3+}$ is in the form of a $(M^{3+})_6$ cluster. In other embodiments, the $(M^{3+})_6$ cluster comprises at least one selected from the group consisting of a $\mu_3$-OH bridging ligand and a $\mu_3$-O bridging ligand.

In certain embodiments, the $M^{4+}$ is in the form of a $(M^{4+})_6$ cluster. In other embodiments, the $(M^{4+})_6$ cluster comprises at least one selected from the group consisting of a $\mu_3$-OH bridging ligand and a $\mu_3$-O bridging ligand.

In certain embodiments, the MOF comprises water. In other embodiments, the MOF comprises ammonium. In yet other embodiments, the MOF comprises dimethylammonium.

In certain embodiments, each $(M^{3+})_6$ cluster is bound to from 4 to 12 tetratopic organic ligands of formula (I). In certain embodiments, each $(M^{3+})_6$ cluster is bound to 12, 8, or 4 tetratopic organic ligands of formula (I).

In certain embodiments, each $(M^{4+})_6$ cluster is bound to from 4 to 12 $H_4ptca$ ligands. In certain embodiments, each $(M^{4+})_6$ cluster is bound to 12, 8, or 4 $H_4ptca$ ligands.

In certain embodiments, the $(M^{3+})_6$ cluster is arranged such that the $M^{3+}$ ions form an octahedron.

In certain embodiments, the $(M^{4+})_6$ cluster is arranged such that the $M^{4+}$ ions form an octahedron.

In certain embodiments, the metal-organic framework crystallizes in a form such that the secondary building units (SBUs) of the material is $Y_6(OH)_8(COO)_{12}(H_2O)_6(DMA)_2$.

In certain embodiments, the at least one ligand of formula (I) is a compound selected from the group consisting of

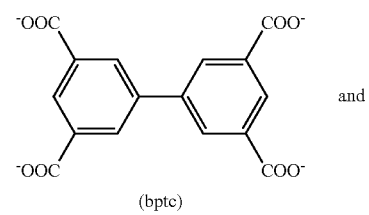

(bptc)

and

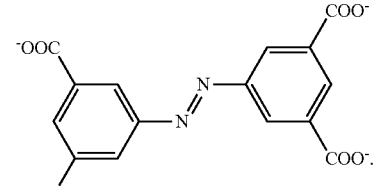

(abtc)

In certain embodiments, the metal-organic framework has a unit formula of selected from the group consisting of $Y_6(OH)_8(abtc)_3(H_2O)_6(DMA)_2$, and $Y_6(OH)_8(bptc)_3(H_2O)_6(DMA)_2$.

In certain embodiments, the metal-organic framework has a ftw or scu topology.

In certain embodiments, the metal-organic framework crystallizes in a cubic crystal system. In other embodiments, the metal-organic framework crystallizes in a cubic crystal system in space group Im3.

In certain embodiments, the metal-organic framework crystallizes in a trigonal crystal system. In other embodiments, the metal-organic framework crystallizes in a trigonal crystal system in space group R-3c.

In certain embodiments, the MOF has a surface area from about 200 m²/g to about 1000 m²/g. In other embodiments, the MOF has a surface area from about 300 m²/g to about 500 m²/g. In yet other embodiments, the MOF has a micropore volume from about 0.05 cm²/g to about 0.50 cm²/g. In yet other embodiments, the MOF has a micropore volume from about 0.10 cm²/g to about 0.25 cm²/g. In certain embodiments, the MOF is thermally stable up to about 400° C.

In certain embodiments, the metal-organic framework 3D structure has a pore or window size of about 4 Å to about 20

Å. In other embodiments, the metal-organic framework 3D structure has a pore or window size of about 4 Å to about 7 Å.

In certain embodiments, the metal-organic framework is a compound of formula $Y_6(OH)_8(abtc)_3(H_2O)_6(DMA)_2$. In other embodiments, the metal-organic framework is a compound of empirical formula $C_{26} H_{27} N_4 O_{19} Y_3$. In yet other embodiments, the metal-organic framework crystallizes in a cubic crystal system in space group R-3c. In yet other embodiments, the metal-organic framework has unit cell dimensions a=18.0682(7) Å, c=45.3244(2) Å. In yet other embodiments, the metal-organic framework has a unit volume of about 12814(1)Å$^3$. In yet other embodiments, the metal-organic framework has an X-ray powder diffraction spectrum comprising 2Θ values (in degrees) of about 6.86, 9.63, 9.78, 11.40, 11.71, 11.96, 13.74, and 15.10. In yet other embodiments, the metal-organic framework of formula $Y_6(OH)_8(abtc)_3(H_2O)_6(DMA)_2$ has a smaller pore or window size than the analogous $Tb^{3+}$ framework. In yet other embodiments, the pore-aperture size is smaller than 4.44× 2.35 Å.

In certain embodiments, the metal-organic framework is a compound of formula $Y_6(OH)_8(bptc)_3(H_2O)_6(DMA)_2$. In other embodiments, the metal-organic framework is a compound of empirical formula $C_{26} H_{27} N O_{19} Y_3$. In yet other embodiments, the metal-organic framework crystallizes in a cubic crystal system in space group Im-3. In yet other embodiments, the metal-organic framework has unit cell dimensions a=25.0883(6) Å. In yet other embodiments, the metal-organic framework has a unit volume of about 15791.15(65) Å$^3$. In yet other embodiments, the metal-organic framework has an X-ray powder diffraction spectrum comprising 2Θ values (in degrees) of about 7.04, 8.63, 9.96, 11.14, 12.21, 13.19, 14.11, and 14.97.

In certain embodiments, the MOF is capable of reversibly and selectively adsorbing aliphatic hydrocarbon compounds. In other embodiments, the MOF is capable of adsorbing alkanes, alkenes, and alkynes, including single, double and triple unsaturated compounds. In other embodiments, the aliphatic hydrocarbon compounds are C2-C7 compounds. In yet other embodiments, the aliphatic hydrocarbon compounds are straight chained, branched, or multi-branched compounds. In an exemplary embodiment, the MOF is capable of reversibly adsorbing propylene. In other embodiments, the MOF is capable of adsorbing from about 20 mg/g to about 100 mg/g of aliphatic hydrocarbon (hydrocarbon/MOF). In yet other embodiments, the MOF is capable of reversibly adsorbing from about 0.5 mmol/g to about 2 mmol/g of propylene (propylene/MOF).

In certain embodiments, the MOF is capable of separating aliphatic hydrocarbon isomers from one another. In other embodiments, the MOF is capable of separating propylene from propane and other larger hydrocarbons. Without wishing to be limited by any particular theory, the MOF is capable of separating propylene from propane through selective adsorption, whereby propane and larger hydrocarbons are not adsorbed or only marginally adsorbed due to size exclusion, and propylene is strongly adsorbed.

Separation Methods

The invention further provides methods of separating aliphatic hydrocarbon compounds from one another using the metal-organic frameworks of the invention. In certain embodiments, the method comprises contacting a mixture of aliphatic hydrocarbons with a MOF of the invention. In other embodiments, the method comprises running a mixture of aliphatic hydrocarbons through a column at is at least partially filled within a MOF of the invention.

In certain embodiments, the mixture of aliphatic hydrocarbon compounds comprise one or more selected from the group consisting of alkanes, alkenes, and alkynes, including single, double and triple unsaturated compounds. In other embodiments, the aliphatic hydrocarbon compounds are C2-C7 compounds. In yet other embodiments, the aliphatic hydrocarbon compounds are straight chained, branched, or multi-branched compounds.

In certain embodiments, the method comprises running a mixture of aliphatic hydrocarbons comprising propylene and propane through a column which is at least partially filled with a MOF of the invention, whereby the propylene is separated from the mixture. In other embodiments, the method comprises running a mixture of C3 compounds through a column comprising a MOF of the invention. In other embodiments, the method comprises running a mixture comprising of propylene and propane through a column comprising a MOF of the invention, whereby the propylene and propane elute from the column at different times.

In certain embodiments, the hydrocarbons are in a gaseous form. In other embodiments, the separation takes place at a temperature from about 25° C. to about 200° C. In yet other embodiments, the separation takes place at a temperature from about 25° C. to about 35° C.

In certain embodiments, the MOF is pre-activated before being used in the separation methods. In other embodiments, the pre-activation comprises heating the MOF to a temperature of about 60° C. to about 300° C.

Kits and Devices

The invention also provides kits and devices comprising the MOF of the invention.

In certain embodiments, the invention provides a device comprising a column which is at least partially filled with a MOF of the invention. In other embodiments, the device is adapted and configured to flow a mixture of hydrocarbons through a column which is at least partially filled with a MOF of the invention. In yet other embodiments, the device is adapted and configured to flow the mixture of gaseous hydrocarbons through the column under an applied pressure.

In certain embodiments, the device is a fix-bed reactor packed with the MOF of the invention. In certain embodiments, the device is capable of separating aliphatic hydrocarbons from one another. In other embodiments, the device is capable of separating propylene gas from propane gas.

In certain embodiments, the invention provides a kit comprising a device of the invention. In other embodiments, the kit comprises instructional materials for operating the device. In yet other embodiments, the kit comprises instructional materials for carrying out the methods of the invention.

Definitions

As used herein, each of the following terms has the meaning associated with it in this section.

As used herein, unless defined otherwise, all technical and scientific terms generally have the same meaning as commonly understood by one of ordinary skill in the art to which this invention belongs. Generally, the nomenclature used herein and the laboratory procedures in surface chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the terms "linker" and "ligand" are used interchangeably to denote a ligand that complexes a metal ion. Further, as used herein, in certain embodiments, the non-ionized ligand (as the corresponding carboxylic acid) and the ionized ligand (as the carboxylate) are used interchangeably in describing the formation of the MOF with the metal ion, under the understanding that the ligand becomes ionized once bound to the metal ion. For example, the invention contemplates that a MOF formed between $Y^{3+}$ and abtc can also be described as a MOF formed between $Y^{3+}$ and $H_4$abtc, and such MOFs should be considered to be identical in the present disclosure.

As used herein, the term "MOF" refers to a metal-organic framework compound comprising metal ions and/or metal clusters coordinated to organic ligands to form one, two or three-dimensional structures. MOFs often contain pores or voids that extend throughout the framework structure. These pores are often stable and can act as hosts in guest-host interactions with guest molecules.

As used herein, the term "Zeolite 4A (LTA)" and "zeolite 4A" refer to a zeolite Linde Type A material having $Ca^{2+}$ and $Na^+$ charge-balancing cations and a pore size of about 4 Å.

As used herein, the term "Zeolite 5A (LTA)" and "zeolite 5A" refer to a zeolite Linde Type A material having $Ca^{2+}$ and $Na^+$ charge-balancing cations and a pore size of about 5 Å.

As used herein, the term "alkenyl," employed alone or in combination with other terms, means, unless otherwise stated, a stable monounsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. A specific example is ($C_1$-$C_3$)alkoxy, such as, but not limited to, ethoxy and methoxy.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. A selected example is ($C_1$-$C_6$)alkyl, such as, but not limited to, ethyl, methyl, isopropyl, isobutyl, n-pentyl, n-hexyl and cyclopropylmethyl.

As used herein, the term "alkynyl," employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—CCH. The term "homopropargylic" refers to a group exemplified by —$CH_2CH_2$—C≡CH. The term "substituted propargylic" refers to a group exemplified by —$CR_2$—C≡CR', wherein each occurrence of R' is independently H, alkyl, substituted alkyl, alkenyl or substituted alkenyl, with the proviso that at least one R' group is not hydrogen. The term "substituted homopropargylic" refers to a group exemplified by —$CR'_2CR'_2$—C≡CR', wherein each occurrence of R' is independently H, alkyl, substituted alkyl, alkenyl or substituted alkenyl, with the proviso that at least one R' group is not hydrogen.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl.

As used herein, the term "alkylene" by itself or as part of another substituent means, unless otherwise stated, a straight or branched hydrocarbon group having the number of carbon atoms designated (i.e., $C_1$-$C_{10}$ means one to ten carbon atoms) and includes straight, branched chain, or cyclic substituent groups, wherein the group has two open valencies. Examples include methylene, 1,2-ethylene, 1,1-ethylene, 1,1-propylene, 1,2-propylene and 1,3-propylene. Heteroalkylene substituents can a group consisting of the stated number of carbon atoms and one or more heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group.

As used herein, the term "alkenylene", employed alone or in combination with other terms, means, unless otherwise stated, a stable mono-unsaturated or di-unsaturated straight chain or branched chain hydrocarbon group having the stated number of carbon atoms wherein the group has two open valencies. Heteroalkenylene substituents can a group consisting of the stated number of carbon atoms and one or more heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkenyl group, including between the rest of the heteroalkenyl group and the fragment to which it is attached, as well as attached to the most distal carbon atom in the heteroalkenyl group.

As used herein, the term "alkynylene", employed alone or in combination with other terms, means, unless otherwise stated, a stable straight chain or branched chain hydrocarbon group with a triple carbon-carbon bond, having the stated number of carbon atoms wherein the group has two open valencies. Heteroalkynylene substituents can a group consisting of the stated number of carbon atoms and one or more heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkynyl group, including between the rest of the heteroalkynyl group and the fragment to which it is attached, as well as attached to the most distal carbon atom in the heteroalkynyl group.

As used herein, the term "halide" refers to a halogen atom bearing a negative charge. The halide anions are fluoride ($F^-$), chloride ($Cl^-$), bromide ($Br^-$), and iodide ($I^-$).

As used herein, the term "halo" or "halogen" alone or as part of another substituent refers to, unless otherwise stated, a fluorine, chlorine, bromine, or iodine atom.

As used herein, the term "substituted" refers to that an atom or group of atoms has replaced hydrogen as the substituent attached to another group.

As used herein, the term "substituted", such as in "substituted alkyl", "substituted alkenyl", "substituted alkynyl", "substituted alkylene", "substituted alkenylene" or "substituted alkynylene" means alkyl, cycloalkyl, alkenyl, alkynyl, alkylene, alkenylene, alkynylene as defined above, substituted by one, two or three substituents selected from the group consisting of $C_1$-$C_{10}$ alkyl, halogen, =O, —OH, alkoxy, tetrahydro-2-H-pyranyl, —$NH_2$, —$N(CH_3)_2$, (1-methyl-imidazol-2-yl), pyridin-2-yl, pyridin-3-yl, pyridin-4-yl, —C(=O)OH, trifluoromethyl, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. Although the description herein contains many embodiments, these should not be construed as limiting the scope of the invention but as merely providing illustrations of some of the presently preferred embodiments of the invention.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application. In general the terms and phrases used herein have their art-recognized meaning, which can be found by reference to standard texts, journal references and contexts known to those skilled in the art. Any preceding definitions are provided to clarify their specific use in the context of the invention.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

General Information

All reagents were used as received unless otherwise specified. $^1$H NMR data were collected on a 300 MHz Oxford NMR unit. X-ray single-crystal data collection of Y-bptc was obtained on a Bruker D8 Venture diffractometer equipped with a graphite monochromator using Mo Kα radiation ($\lambda$=0.71073 Å) at 173 K. A multiscan technique was used to perform adsorption corrections. The crystal structure was solved using direct methods and refined using the full matrix least-squares method on $F^2$ with anisotropic thermal parameters for all non-hydrogen atoms using the SHELXL-2014 program. All hydrogen atoms were located in calculated positions and refined isotropically. Powder X-ray diffraction patterns were recorded on a Ultima IV with Cu Kα radiation ($\lambda$=1.5406 Å). Data were collected at room temperature at 2θ=3–40° with a scan speed of 2°/min and operating power of 40 kV and 44 mA. For structure solution process, PXRD data were collected on a Bruker AXS D8 Advance diffractometer (see Thermodiffractomery). Thermogravimetric analysis was carried out on a Q5000 (TA Instruments) analyzer. For each run 3-4 mg of sample was heated from room temperature to 600° C. at a ramp rate of 10° C./min. $N_2$ adsorption experiments at 77 K and $CO_2$ adsorption measurements at 195 K were performed on a Micromeritics 3Flex adsorption analyzer with liquid nitrogen and dry ice/isopropanol as coolants, respectively. Prior to each measurement, ~100 mg of solvent exchanged sample was activated at 200 or 300° C. under dynamic vacuum overnight.

Synthesis of $H_4$bptc

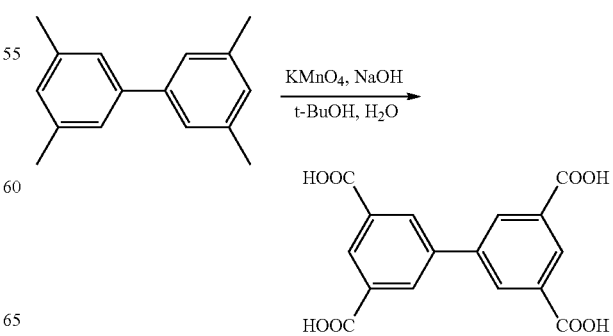

3,3'5,5'-tetramethylbiphenyl (5.0 g, 0.023 mol), and NaOH (2.0 g, 0.05 mol) were mixed in t-BuOH/H₂O (100 mL/100 mL) with stirring at 50° C. KMnO₄ (43.0 g, 0.27 mol) was added in portions over one week. The temperature was subsequently increased to 70° C. and kept for 2 days. The mixture was filtered when hot and the clear filtrate was added into 100 mL of 6M HCl. White solid was obtained upon filtration. The crude product was recrystallized from DMF (~100 mL) to give pure H₄bptc with a yield of 82%. ¹H NMR (400 MHz, DMSO-d⁶): δ=13.50 (4H, COOH), 8.51 (2H, Ar—H), 8.42 (4H, Ar—H).

Synthesis of H₄abtc

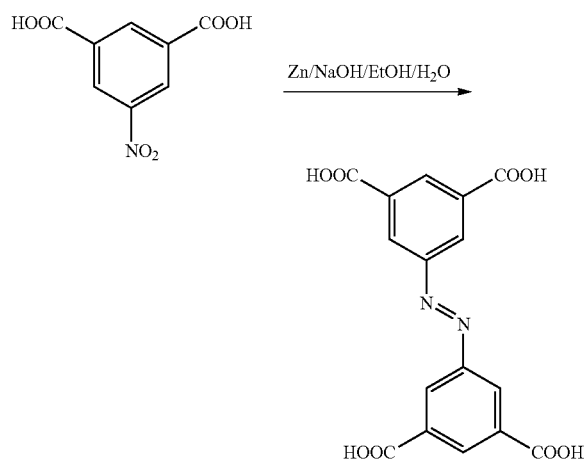

5-nitroisophthalic acid (2.1 g, 0.01 mol), NaOH (3.2 g, 0.08 mol), and zinc powder (2.1 g, 0.04 mol) were mixed in ethanol/H₂O (50 mL/20 mL). The mixture was kept under reflux for 12 hours before being cooled to room temperature. Yellow solid was obtained through vacuum filtration which was then dissolved in 80 mL 1M NaOH solution. Upon filtration, the filtrate was acidified with 6 M HCl to get orange solid. The crude product was recrystallized from DMF to give pure H₄abtc as an orange solid (1.3 g, yield: 73%). ¹H NMR (400 MHz, DMSO-d⁶): δ=13.38 (4H, COOH), 8.58-8.61 (6H, Ar—H).

Synthesis of Y-bptc

Y(NO₃)₃.6H₂O (38.3 mg, 0.1 mmol) and 2-fluorobenzoic acid (1.0 g, 4.1 mmol) were dissolved in DMF/H₂O (5 mL/2 mL) in a 20 mL glass vial and H₄bptc (16.5 mg, 0.05 mmol) was added to the solution. The mixture was sonicated for 5 minutes before being placed in 120° C. oven for 3 days. Colorless cubic crystals were obtained by filtration. The crystals were washed with DMF (3×5 mL) and then immersed in 5 mL of acetone for one week during which the solvent was replaced twice a day. The solvent-exchanged sample was dried at 200° C. under vacuum to yield activated sample. 50× scaled up synthesis resulted in materials with similar crystallinity.

Synthesis of Y-abtc

Y(NO₃)₃.6H₂O (38.3 mg, 0.1 mmol) and 2-fluorobenzoic acid (1.5 g, 6 mmol) were dissolved in DMF/H₂O (5 mL/2 mL) in a 20 mL glass vial and H₄abtc (17.5 mg, 0.05 mmol) was added to the solution. The mixture was sonicated for 5 minutes before being placed in 120° C. oven for 3 days. Orange cubic crystals were obtained by filtration. The crystals were washed with DMF (3×5 mL) and then immersed in 5 mL methanol for one week during which the solvent was replaced twice a day. The solvent-exchanged sample was dried at 200 or 300° C. under vacuum to yield activated sample. 50× scaled up synthesis resulted in material with similar crystallinity.

Thermodiffractomery

Figure 16:
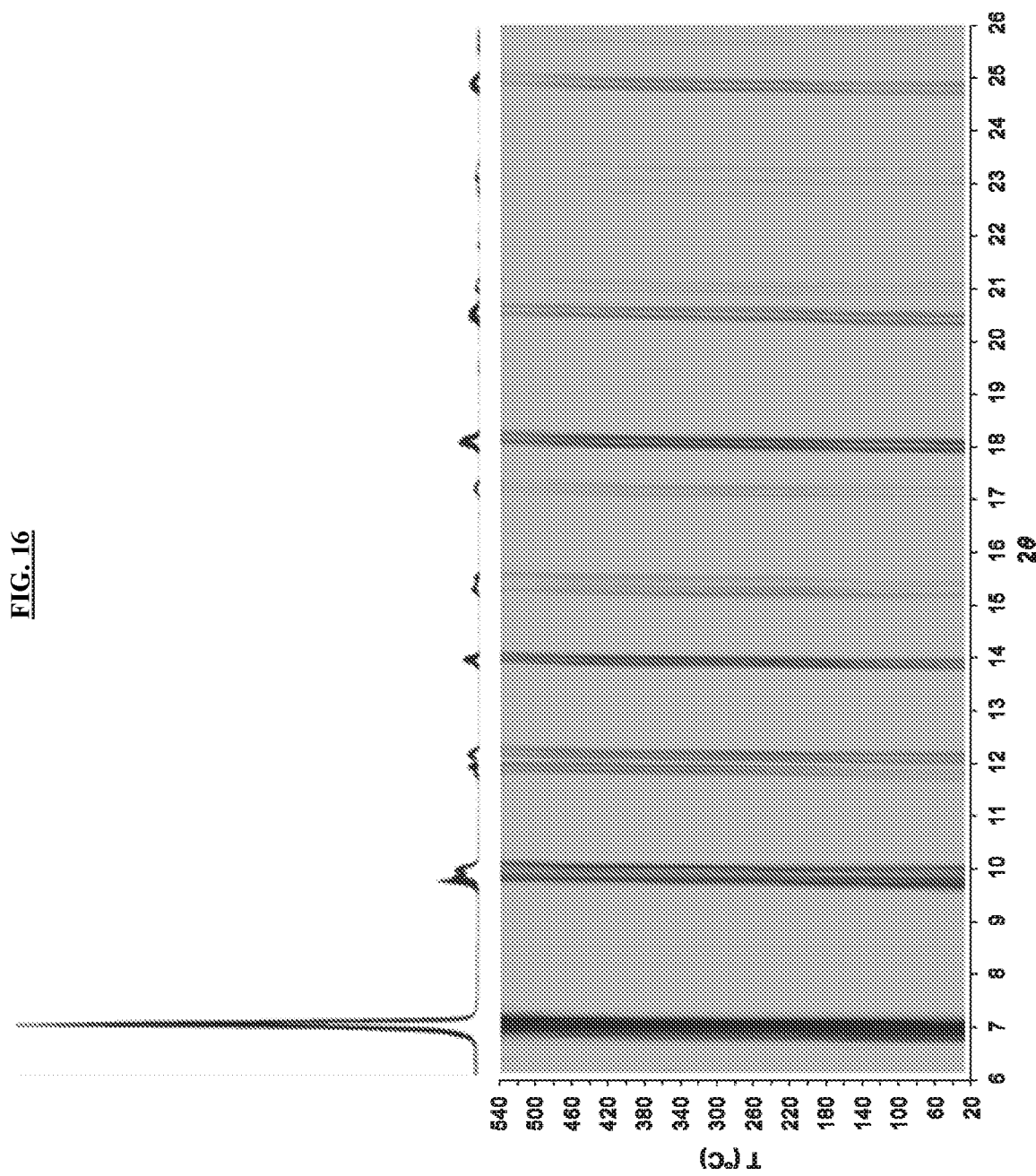
FIG. 16 illustrates a head-on overlaid powder X-ray diffraction patterns measured at elevating temperatures in the range 20-540° C. for Y-abtc (top) and its two-dimensional contour plot as a function of 2θ and temperature (bottom), displaying the thermal stability. The diffraction patterns remained unaltered during the measurements except for minor changes in peak intensity.
Figure 17:
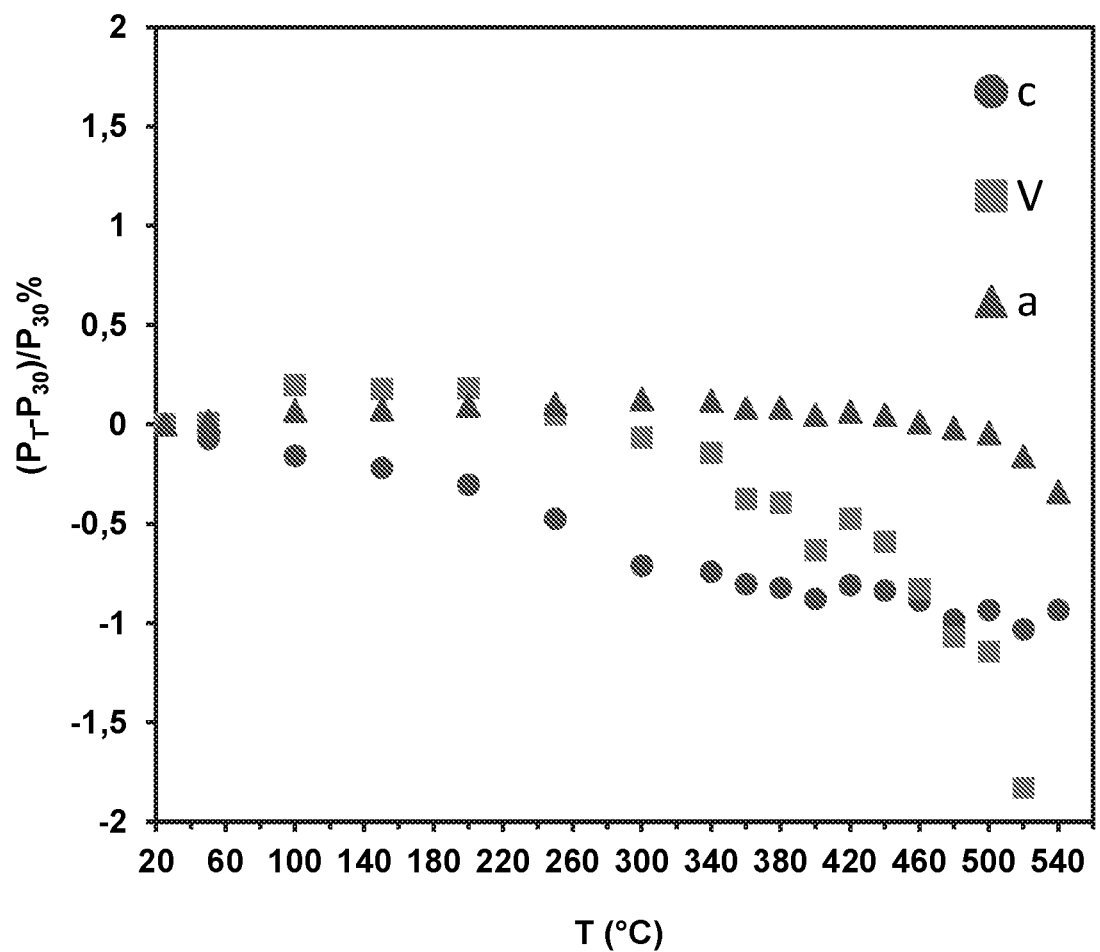
FIG. 17 illustrates a graph showing the variation of the unit cell parameters ($P_T$), normalized to the value at 30° C. ($P_{30}$), as a function of the temperature in the range 30-540° C. a, blue triangles; c, red circles; V, green squares. This graph shows that the framework is substantially rigid, only a small (−2%) volume contraction is observed up to 520° C. (temperature at which the framework start losing its crystallinity).

Variable-temperature X-ray powder diffraction (VT-PXRD) experiments were performed on Y-abtc. The experiment was carried out under N₂ flux by coupling a custom-made sample heater, assembled by Officina Elettrotecnica di Tenno, Ponte Arche, Italy, to the instrumental set-up described in General Information. A powdered microcrystalline sample of Y-abtc was ground in an agate mortar and deposited in the hollow of on a quartz zero-background plate framed by an aluminum skeleton. The data was acquired within a low-angle 2θ range (9-30°), while heating the samples in situ in a temperature range of RT-540° C., with steps of 20° C., under nitrogen flux. The N₂ atmosphere on the sample was insured by a dome that fitted on the sample holder that allowed the X-rays to reach the sample through Kapton windows. Le Bail parametric refinements on the data measured in the range 30-540° C. (i.e. before a significant loss of crystallinity was observed) allowed the behavior of the unit cell parameters to be measured as a function of the temperature. The VT diffractograms and the results of the parametric data treatments are depicted in FIGS. 16-17 and discussed elsewhere herein (see Structural analysis process).

The thermocouple of the VT-PXPD set-up was not in direct contact with the sample. This caused a slight difference in the temperature measurements between the TGA and VT-XRPD during the same event detected by the two techniques. Without intending to be limited to any particular theory, the TGA temperatures are generally considered to be more reliable.

Hydrocarbon Adsorption Measurements

Hydrocarbon adsorption isotherms were collected with a volumetric gas sorption analyzer, Autosorb-1 (Quantachrome Instruments). Analysis temperature (25-80° C.) was controlled by a circulating-bath temperature controller. For a typical isotherm, around 150 mg of the solvent-exchanged sample was used and activated prior to data collection. Hydrocarbon adsorption rate measurements were performed on a gravimetric adsorption unit modified from a Q50 thermogravimetric analyzer (TA Instruments). For each measurement, ~20 mg of MOF sample was activated under nitrogen flow for 2 hours to remove any residual solvent. After cooling down to the adsorption temperature, hydrocarbon flow was mixed with a pure nitrogen stream and then introduced to the adsorption chamber, maintained at analysis temperature. Hydrocarbon partial pressure was controlled by adjusting the relative flow rates of the two gas streams (pure nitrogen and pure hydrocarbon). Sample weight was recorded throughout the process in order to determine the adsorbed amount of the adsorbate.

Column Breakthrough Experiments

Multicomponent column breakthrough experiments were conducted using a lab-scale fix-bed packed with the MOF sample. For a typical experiment, 1.0 g of MOF material was packed into a quartz column (5.8 mm I.D.×150 mm) with silane treated glass wool filling the void space. A helium flow was used for initial purging of the adsorbent. The MOF powder was activated at 200° C. overnight and the helium flow was then turned off while propane and propylene flows were introduced. Flow rates of each gas were adjusted to control the composition of the feed gas mixture. The effluent from the column was monitored using an online GC equipped with HP-PONA column and FID. The absolute adsorbed amount of gas i ($q_i$) is calculated from the breakthrough curve by the equation:

$$q_i = \frac{F_i \times t_0 - V_{dead} - \int_0^{t_0} F_e \Delta t}{m}$$

where Fi is the influent flow rate of the specific gas (cm³/min); $t_0$ is the adsorption time (min); $V_{dead}$ is the dead volume of the system (cm³); $F_e$ is the effluent flow rate of the specific gas (cm³/min); and m is the mass of the sorbent (g).

Ab Initio Structure Solution from Powder XRD Data

Gently ground powders of Y-abtc compound were deposited in the 2 mm deep hollow of a zero background plate (a properly misoriented quartz monocrystal). Diffraction experiments were performed using Cu—Kα radiation (λ=1.5418 Å) on a vertical-scan Bruker AXS D8 Advance diffractometer in θ:θ mode, equipped with a Goebel Mirror and a linear Position Sensitive Detector (PSD), with the following optics: primary and secondary Soller slits, 2.3° and 2.5°, respectively; divergence slit, 0.1°; receiving slit, 2.82°. Generator setting: 40 kV, 40 mA. The nominal resolution for the present set-up is 0.08° 2θ (FWHM of the α1 component) for the LaB$_6$ peak at about 21.3° (2θ). The accurate diffraction patterns at RT and under nitrogen flow were acquired in the 5-105° 2θ range, with Δ2θ=0.02° and an exposure time of 10 s/step with the same chamber used for the thermodiffraction experiments (vide infra) (see Thermodiffractomery).

Structural Analysis Process

Figure 11:
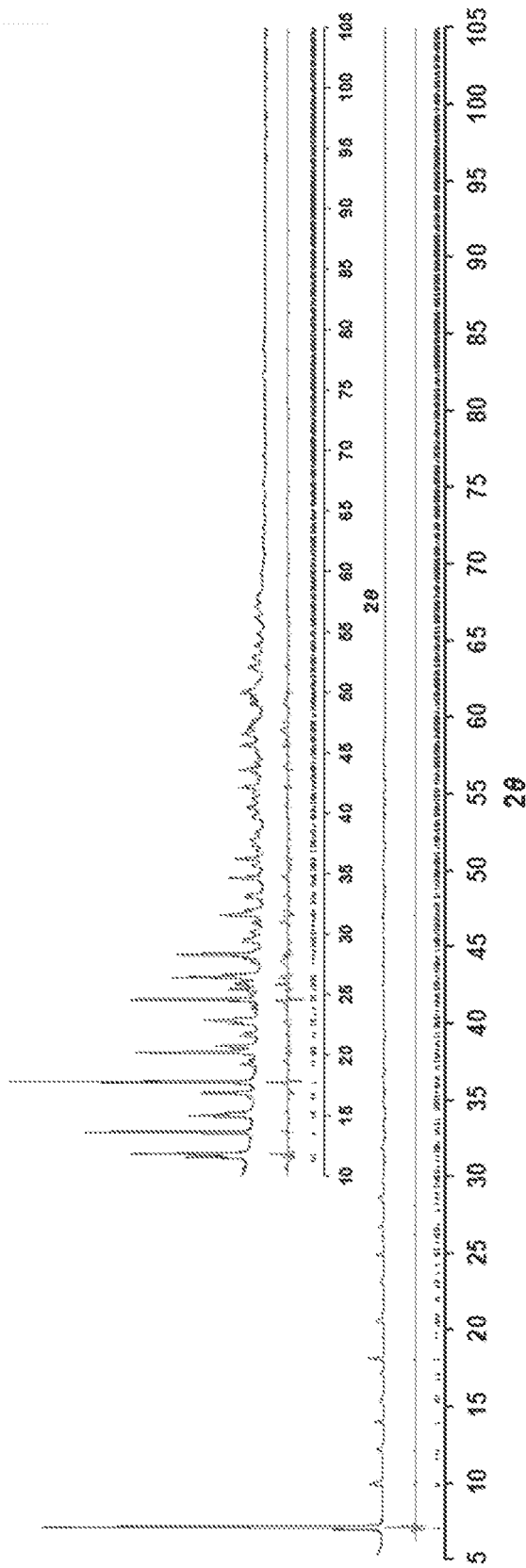
FIG. 11 illustrates a Final Rietveld Refinement plot for Y-abtc. Blue line, experimental data; red line, calculated; gray line, difference between experimental and calculated patterns. Blue tick marks represent peaks positions. The inset show a magnification of the high angle region. $R_p$ and $R_{wp}$=0.0754 and, 0.1022 for 5001 data collected in the 5–105° 2θ range. $R_{Bragg}$=2.22.
Figure 12A:
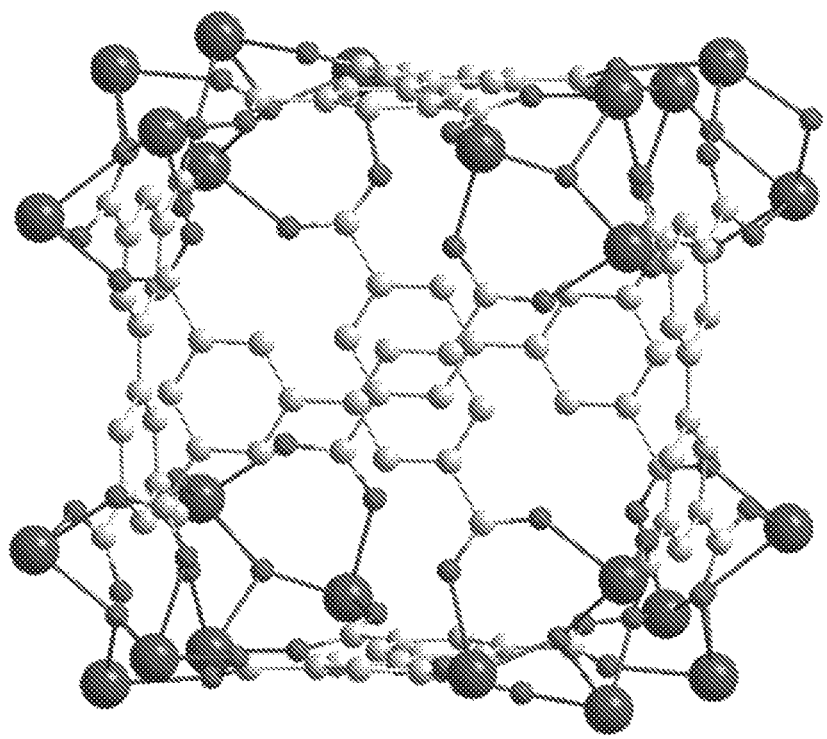
FIGS. 12A-12D illustrate diagrams showing the crystal structure of a single cage and the shape of the cage depicted by connecting eight equivalent $μ_3$-O atom from the vertexes of the cage for Y-abtc (FIGS. 12A-12B) and Y-bptc (FIGS. 12C-12D).
Figure 12B:
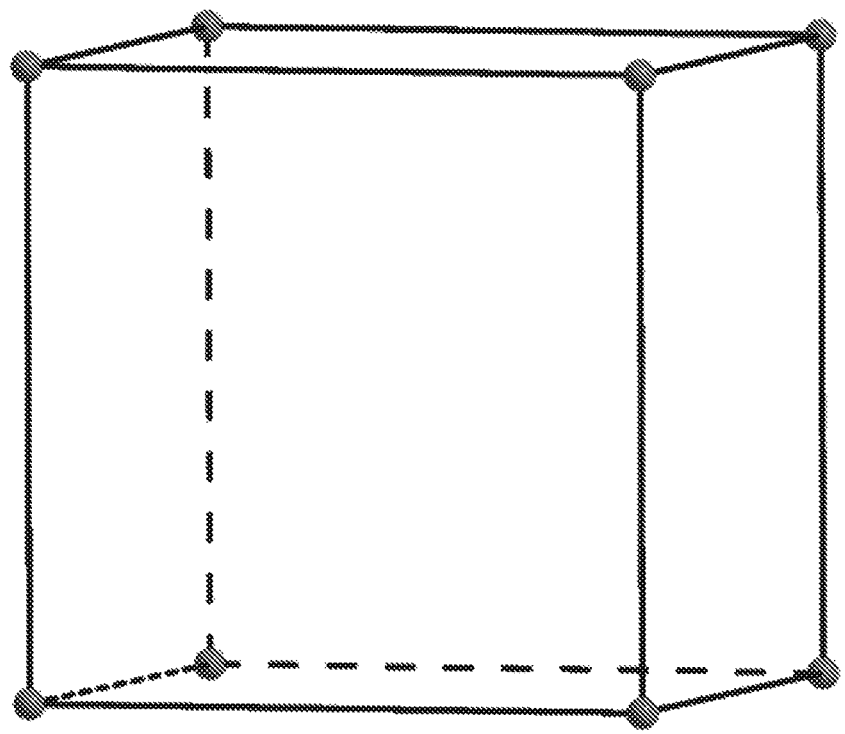
Figure 12C:
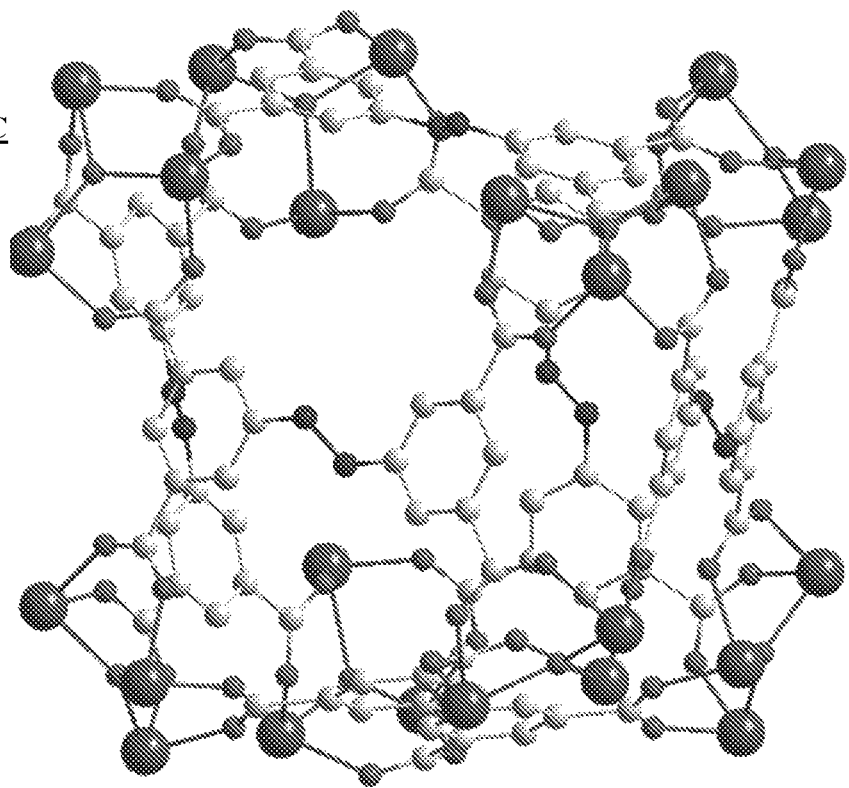
Figure 12D:
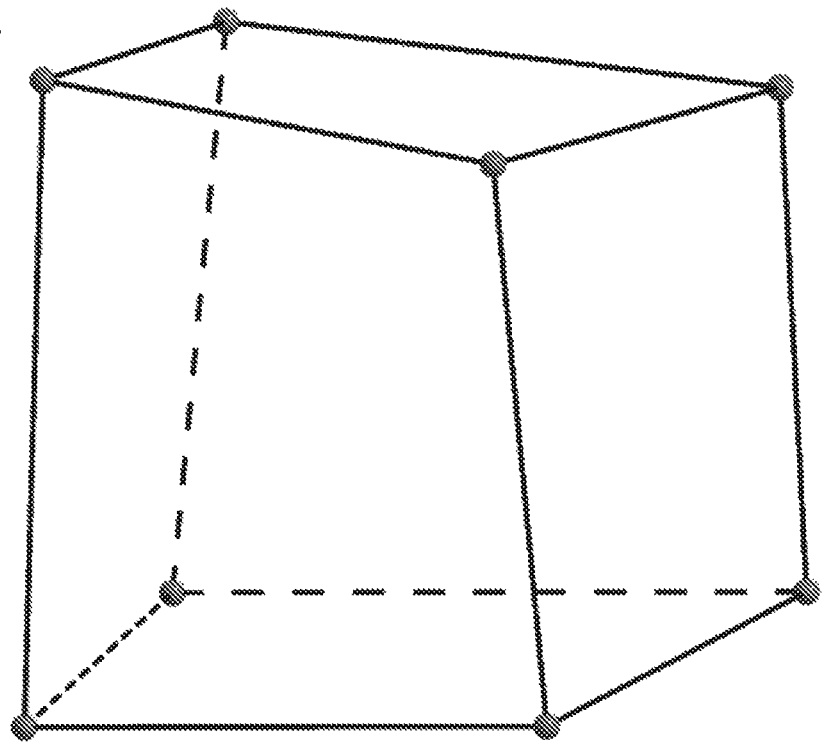
Figure 13A:
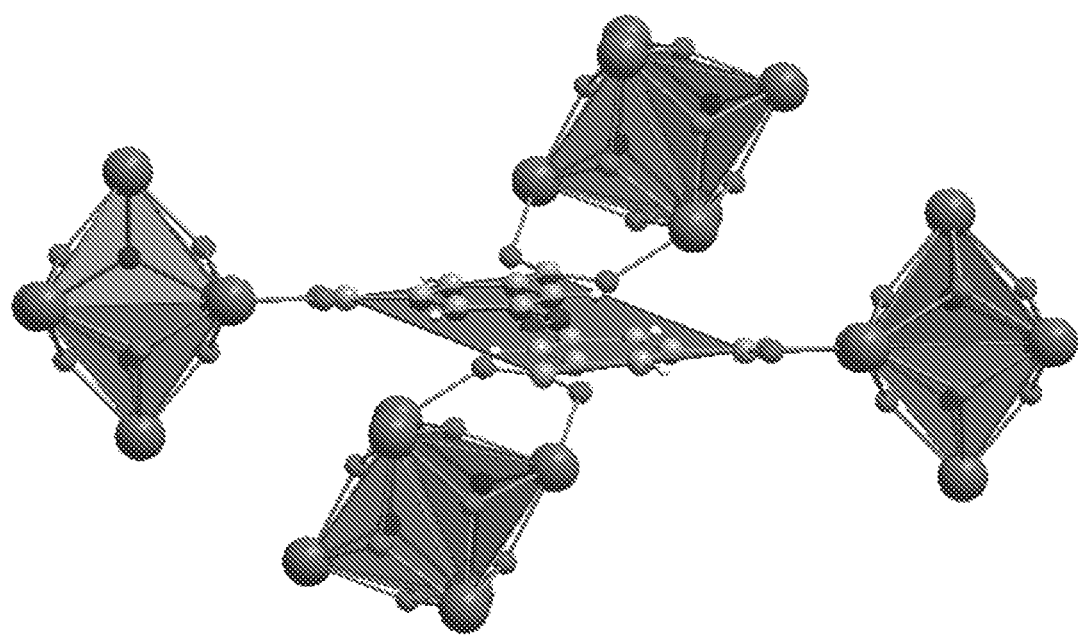
FIGS. 13A-13E illustrate diagrams showing the coordination geometry of abtc and the distortion of the cages in Y-abtc. The 3 fold axis is represented by the fragmented diagonal line in FIGS. 13B-13C.
Figure 13B:
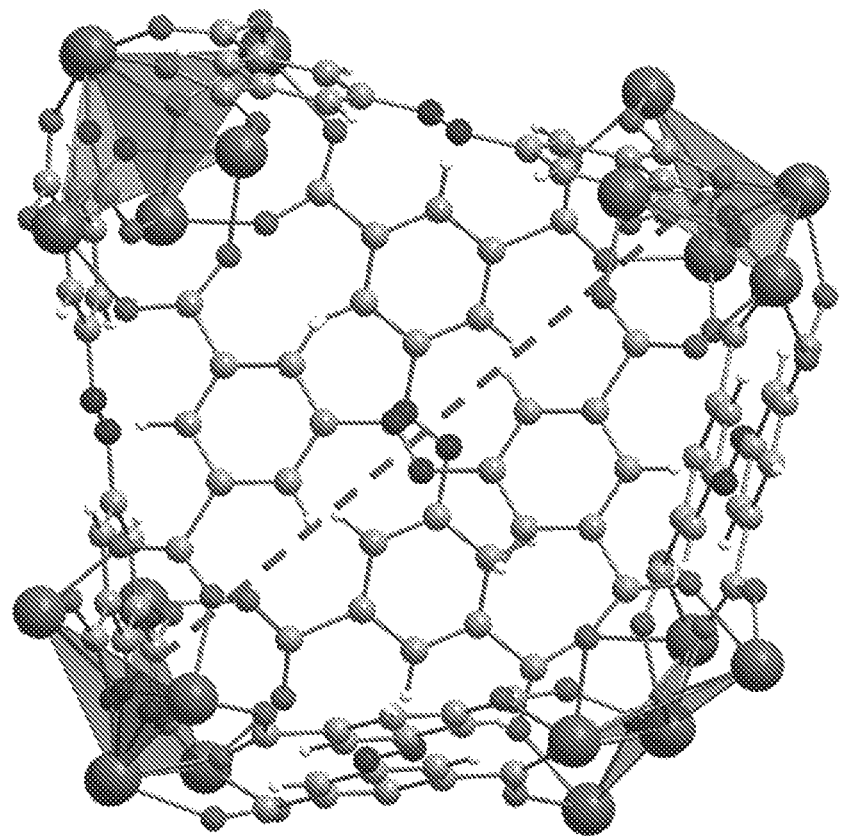
Figure 13C:
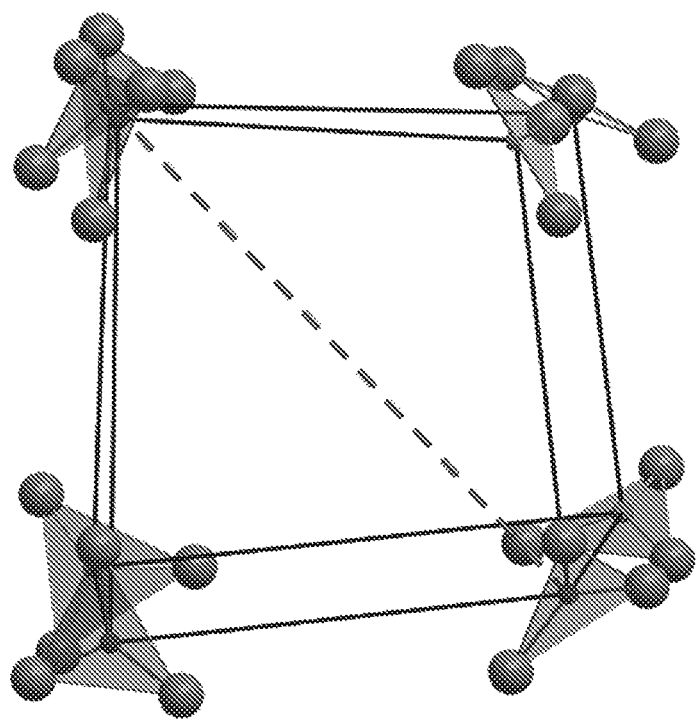
Figure 13D:
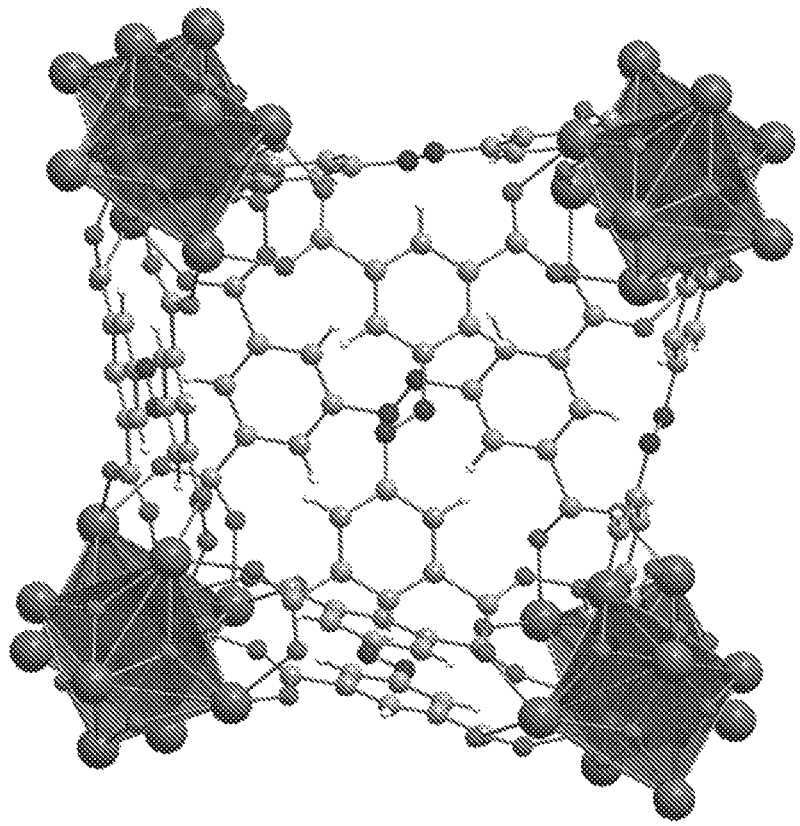
Figure 13E:
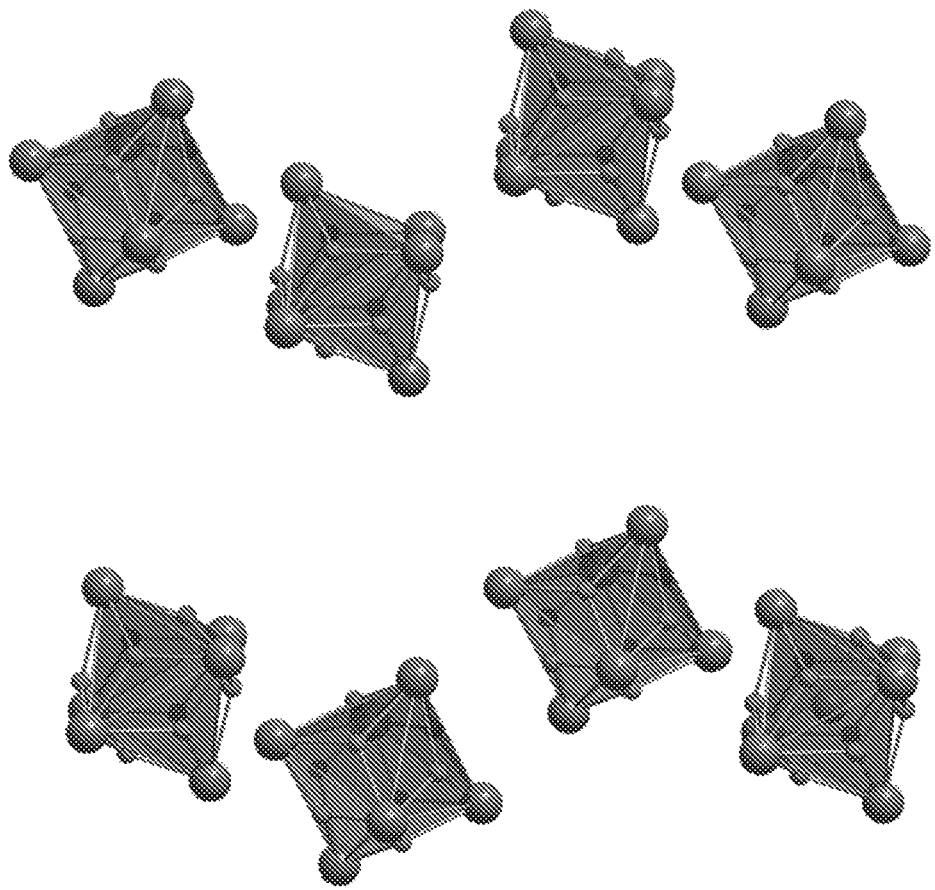

A standard peak search below 30° was followed by indexing through the singular value decomposition method, implemented in TOPAS, which led to a rhombohedral cell of approximate dimensions: a=18.09 Å, b=45.36 Å, c=10.84 Å and V=12860 Å³ (GOF(20)=28.77). A Le Bail refinement of the pattern in R-3 gives rise to a slightly better $R_{wp}$ than in R-3c. However, all peaks were already correctly described by the R-3c space group. Without intending to be limited to any particular theory, the slightly better fitting for R-3 is potentially due to the presence of unobserved peaks that contributed only to the modelling of the background. The determination of the background, correct unit cell parameters, sample displacement and profile parameters to be used in the subsequent simulated annealing runs, was done on the basis of these structure-less Le Bail refinements. The correctness of the R-3c space group was confirmed by the successful two-step simulated annealing approach. In the first run, the [Y$_6$(µ$_3$-OH)$_8$] moiety was localized, centered around a Wyckoff position b, and described by one Y and one O atom in general position and another O atom on a three-fold axis (Wyckoff site c). In the second step, the position of the abtc ligand was located by using a flexible rigid body (FIG. 13A) consisting of the full ligand with halved occupancy, with its center of mass on a d Wyckoff site. Once confirmed to be the right position of the ligand, this was better described by half ligand with full occupancy. The obtained structural model, while coherent for atom connectivity and congruency with the Y-bptc cubic MOF, yielded a high $R_{wp}$=30. Without intending to be limited to any particular theory, this result can be ascribed to the high porosity of the Y-abtc MOF, in which the voids are, in the as synthesized form, filled by solvent molecules and dimethyl ammonium cations, that contributes to the overall intensity of the diffraction peaks. In order to derive data from a partially activated sample, a first quick thermodiffraction experiment (FIGS. 16-17)was performed, with heating steps of 50° C. from RT to 320° C., under N$_2$ flux. The temperature was than kept at 320° C. for 5 hours and the powder was cooled to room temperature for a new overnight scan (by keeping the N$_2$ flux on the sample). The same structural model, refined on the new data set, yielded a $R_{wp}$ of 13.12. A subsequent Rietveld refinement with freely floating water oxygen atoms, with a refinable site occupancy factor, revealed the presence of the oxygen of the coordinated water molecule (with occupancy 0.52) at the Y site. Moreover, the contemporary presence of residual electron density into the voids was described by freely roto-translating dummy C atoms, with refinable occupancy, with the aim of simulating the presence of the extra framework cations. This allowed for the refinement of the powder diffraction pattern to $R_{wp}$=11.41. During these Rietveld refinement steps, torsional angles around the C1-N1; C5-C8 and C3-C7 bonds were allowed to refine. Peak shapes were described with the fundamental parameters approach and with the aid of 4$^{th}$-order spherical harmonics. The background was modelled by a Chebyshev polynomial function. The thermal effect was simulated by using a single isotropic parameter for the metal ion, augmented by 2.0 Å² for lighter atoms. The final Rietveld refinement plot are shown in FIG. 11.

Crystal Data for Y-bptc

Cubic crystal system, space group Im-3, a=25.0883(6) Å, V=15791.15(65) Å³, Z=8. $\rho_{calc}$=1.46718 g·cm⁻³. CCDC No: 185312.

Crystal Data for Y-abtc

Trigonal crystal system, space group R-3c, a=18.0682(7) Å, c=45.3244(2) Å, V=12814(1) Å³, Z=8. $\rho_{calc}$=1.457(3) g·cm⁻³, µ(Cu—K$_α$)=59.5(2) cm⁻¹. $R_p$ and $R_{wp}$=0.0754 and, 0.1022 for 5001 data collected in the 5-105° 2θ range. $R_{Bragg}$=2.218. CCDC No.: 1856158.

Example 1: Metal-Organic Framework Design and Synthesis

A topology-guided construction of Zr-MOFs built on tetratopic carboxylate ligands and their uses for the separation of C6 alkane isomers was previously described in U.S. Provisional Patent Application No. 62/627,297, filed Feb. 7, 2018, incorporated herein by reference, in its entirety. The Zr$_6$O$_8$ building block structural topology depended on the connectivity of the Zr$_6$ clusters and the geometry of the organic ligands used. Three different structures with ftw, scu, and lvt topology were obtained and the connectivity of the Zr6 cluster and the topology of the resulting Zr-MOFs were closely related to the shape (i.e. aspect ratio) of the organic ligand. The use of the smallest ligand, bptc, led to the formation of a ftw type structure with 12-connected Zr6 cluster (Zr-bptc). Without intending to be limited to any particular theory, structures with ftw topology are particularly favorable for molecular separation as they feature large cages connected through small windows. The pore aperture was mainly regulated by the size of the organic ligand (i.e. distance between adjacent carboxylates). Zr-bptc showed optimal pore aperture for the separation of alkane isomers as it adsorbed linear alkanes only and excludes any branched isomers.

Figure 1B:
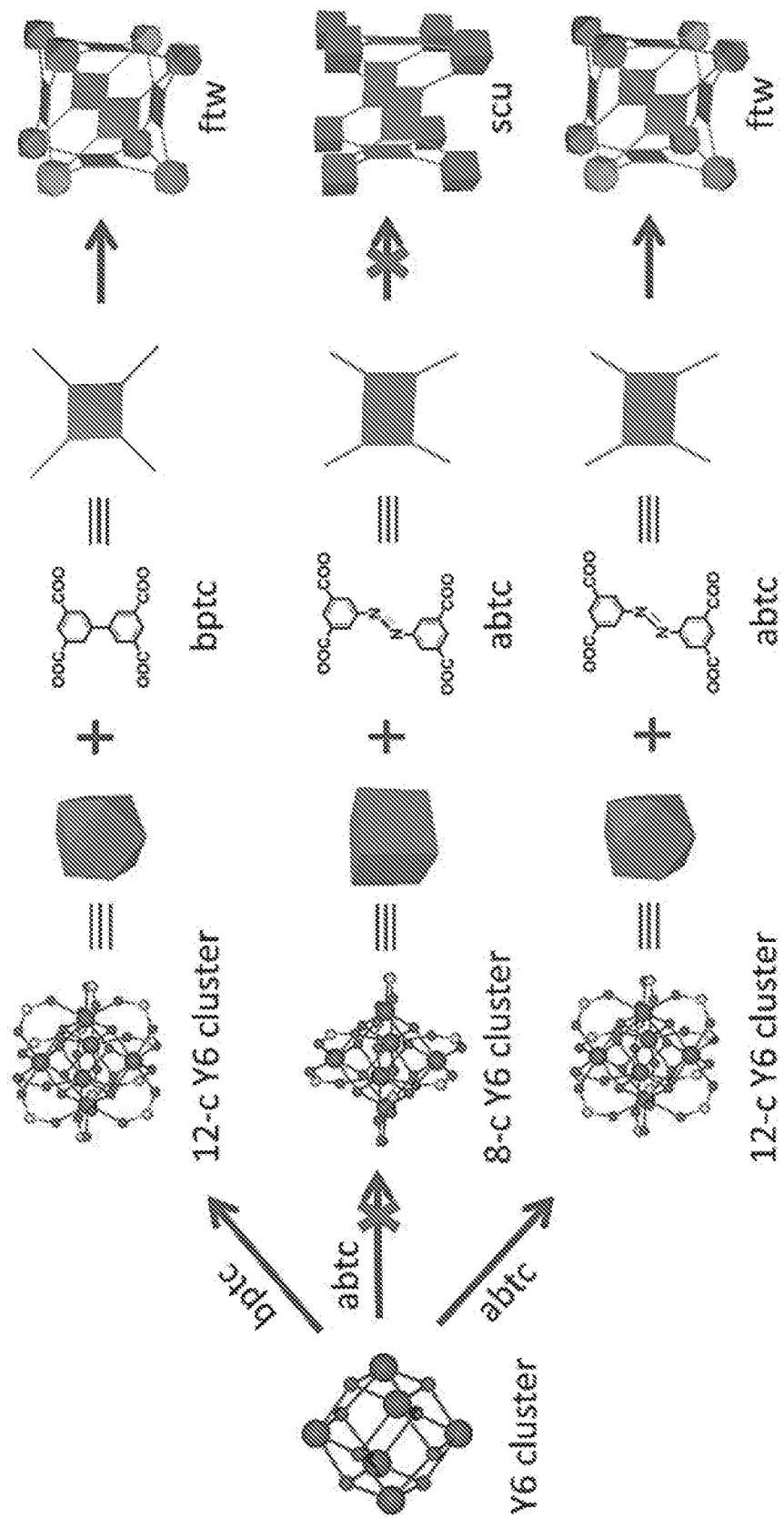

Based on these results, similar structures with slightly reduced pore size were explored in order to find MOFs that are suitable for discriminating between linear paraffins and olefins such as propane and propylene. This was found to be difficult to achieve by simply replacing bptc with an even shorter ligand because bptc, comprised of just two linked isophthalates, is one of the smallest possible organic ligands suited for the construction of ftw type structure. Instead, the inorganic building unit was changed while maintaining the overall connectivity and topology. A careful screening analysis suggests that Y6 cluster, which resembles the Zr6 cluster with respect to composition, geometry, and connectivity had the desired properties. Y6 clusters connect to carboxylate ligands in a similar fashion as that of Zr6 in Zr-MOFs, and form structures with identical topology to that of the latter with the same organic ligands (FIGS. 1A-1B). However, due to the negative charge of the 12-connected cluster $[Y_6(OH)_8(H_2O)_6(COO)_{12}]^{2-}$ and the propagated framework, balancing cations are required in the structure, which can act as a regulatory factor for fine control and pore dimensions adjustments. For a given organic ligand, the presence of charge balancing cations in the Y6 based MOF slightly reduces the effective pore size compared to its analogous structure built on Zr6 cluster.

Figures 7A, 7B:
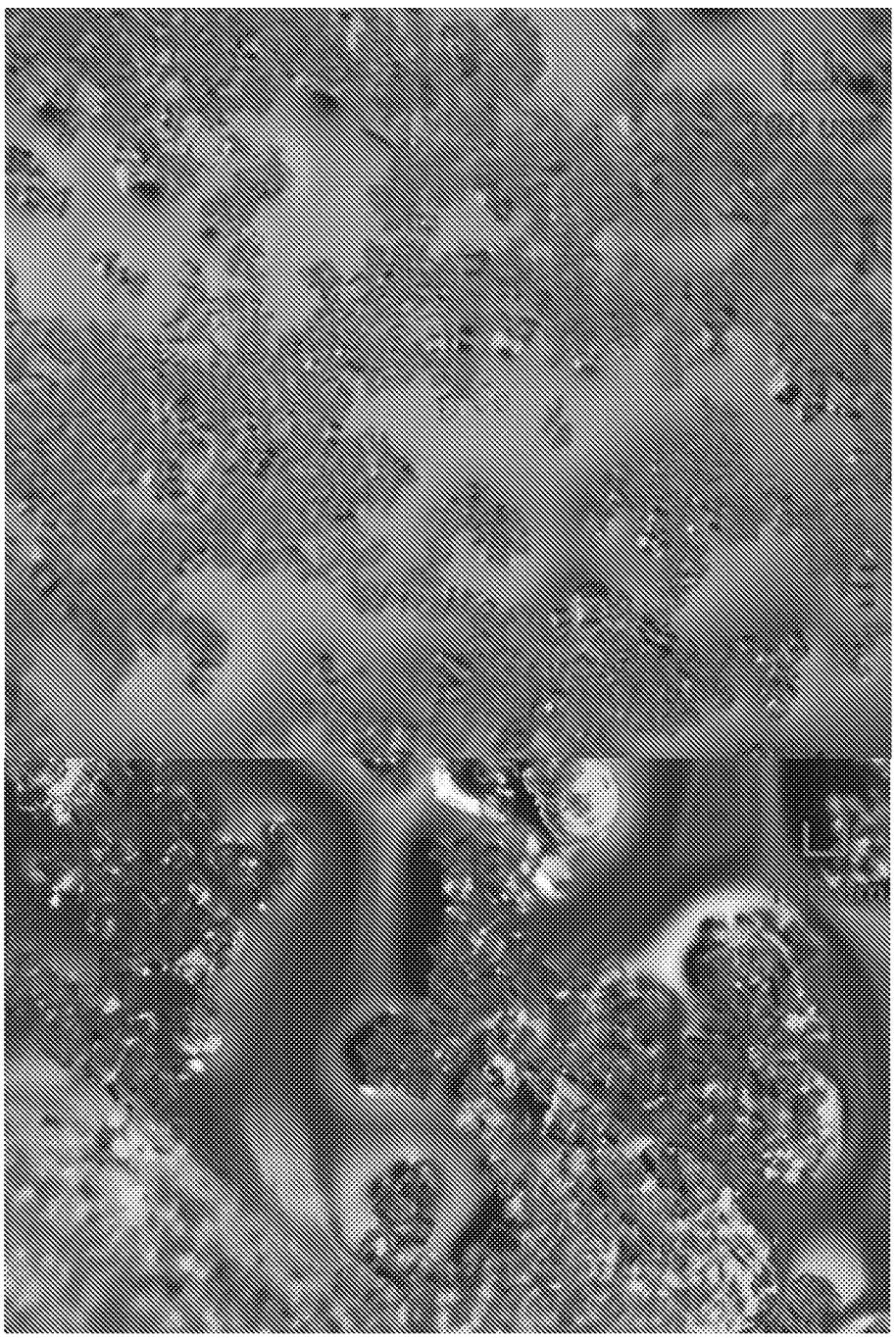
FIGS. 7A-7B illustrate microscopic images of crystals of Y-bptc (FIG. 7A) and Y-abtc (FIG. 7B).
Figure 8:
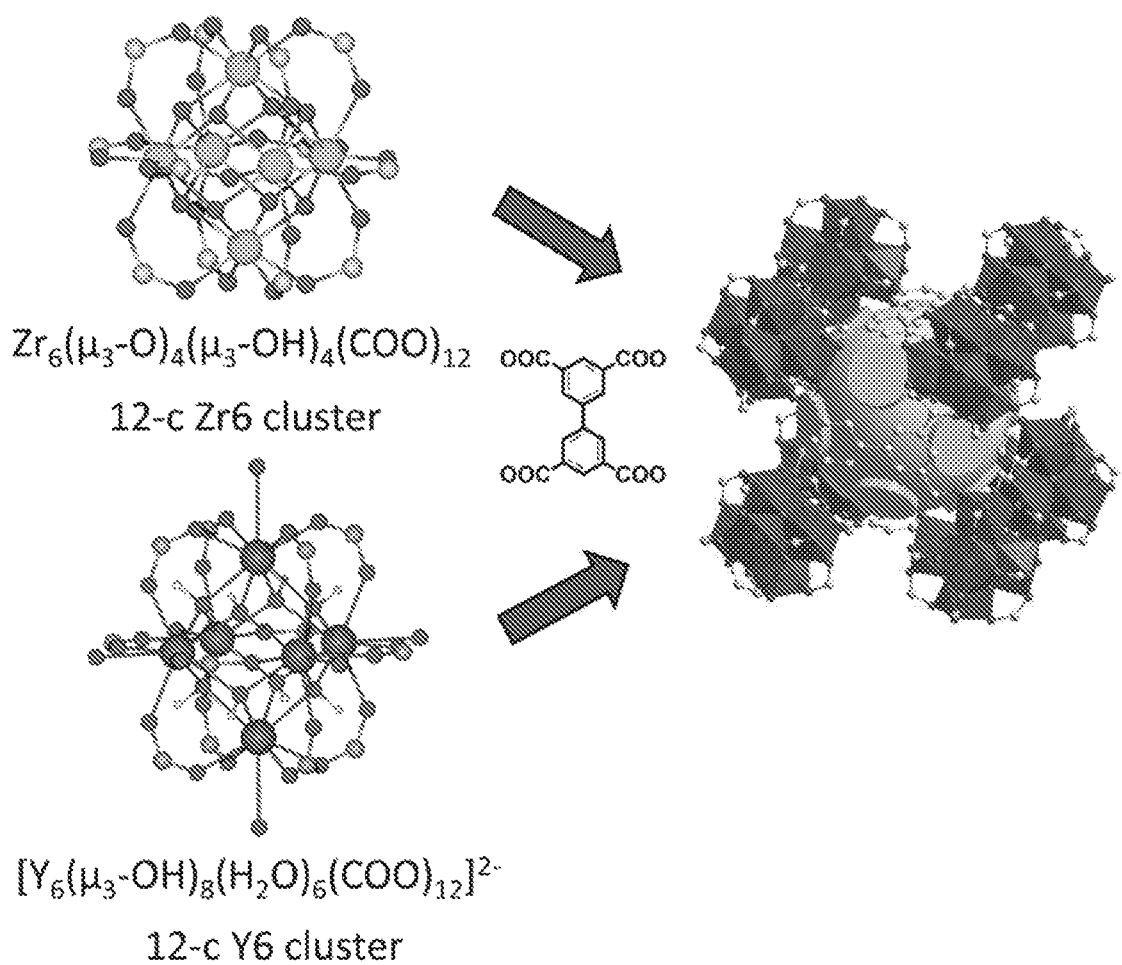
FIG. 8 illustrates a scheme comparing Zr-bptc and Y-bptc. They are both built on 12-connected hexanuclear SBU and share similar connectivity and topology, but the two inorganic clusters are different in terms of composition and coordination.
Figure 9:
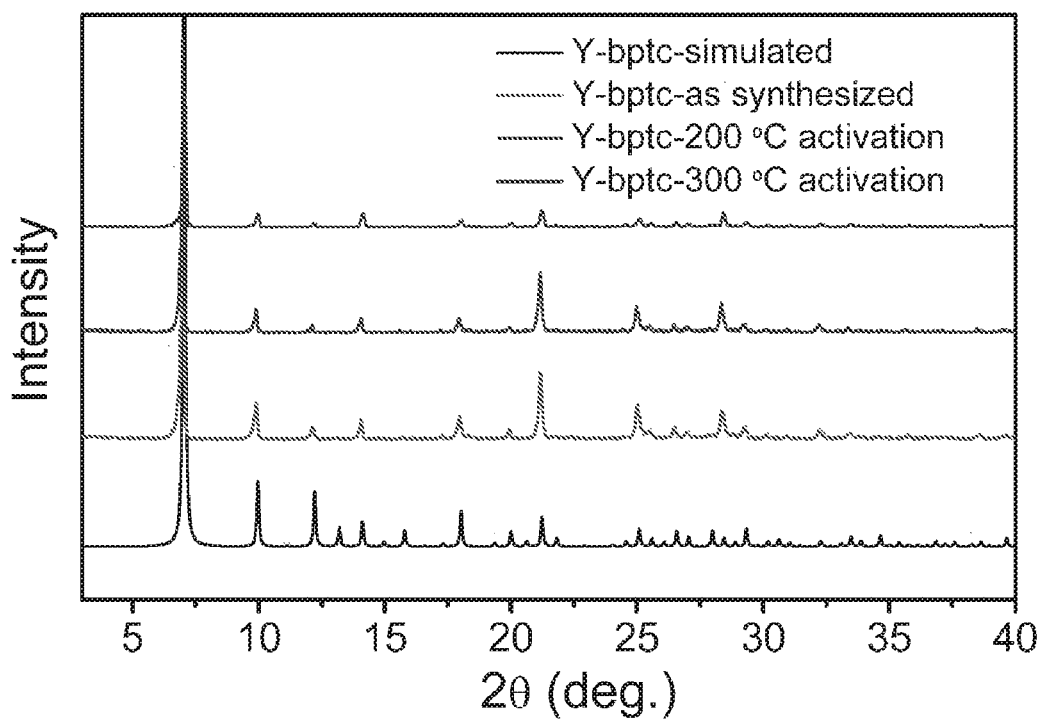
FIG. 9 illustrates a PXRD pattern for Y-bptc.

Y-MOFs were synthesized using $H_4$bptc to produce MOFs having a ftw structure analogous to Zr-bptc but with slightly smaller pore apertures. Colorless cubic crystals of Y-bptc were successfully obtained via solvothermal reactions of $Y(NO_3)_3 \cdot 6H_2O$ and $H_4$bptc in a mixed solvent of DMF and water, using 2-fluorobenzoic acid as an acidic modulator (FIG. 7A). Single crystal X-ray diffraction analysis reveals that Y-bptc crystallized in the cubic Im-3 space group. The structure was built on 12-connected $[Y_6(OH)_8(H_2O)_6(COO)_{12}]^{2-}$ SBU with six $Y^{3+}$ ions assembled into an octahedron where $\mu_3$-OH$^-$ anions occupy the eight facets of the octahedron (FIG. 8). Each $Y^{3+}$ ion was nine coordinated, connecting to four oxygen atoms from four different carboxylate groups, four bridging $\mu_3$-OH$^-$ anions, and one terminal water molecule. The inorganic cluster was slightly different from the commonly observed 12-connected $Zr_6O_4(OH)_4(COO)_{12}$. Due to the lower positive charge of $Y^{3+}$ compared to $Zr^{4+}$, the four bridging $\mu_3$-O$^{2-}$ in Zr-MOFs are replaced by $\mu_3$-OH$^-$ in Y-analogues. The Y6 cluster is negatively charged while the analogous Zr6 cluster is neutral. In addition, each $Y^{3+}$ was coordinated to an additional terminal water, which was not observed for Zr-based structures. The overall connectivity of Y-bptc was otherwise identical to that of Zr-bptc, forming the expected ftw type structure. Y-bptc contained cubic cage-like pores with Y6 clusters on the vertices and bptc$^{4-}$ ligands on the faces, and the cages are interconnected through small windows (FIGS. 1A-1B). The phase purity of Y-bptc was confirmed by powder X-ray diffraction analysis (FIG. 9).

Figure 2:
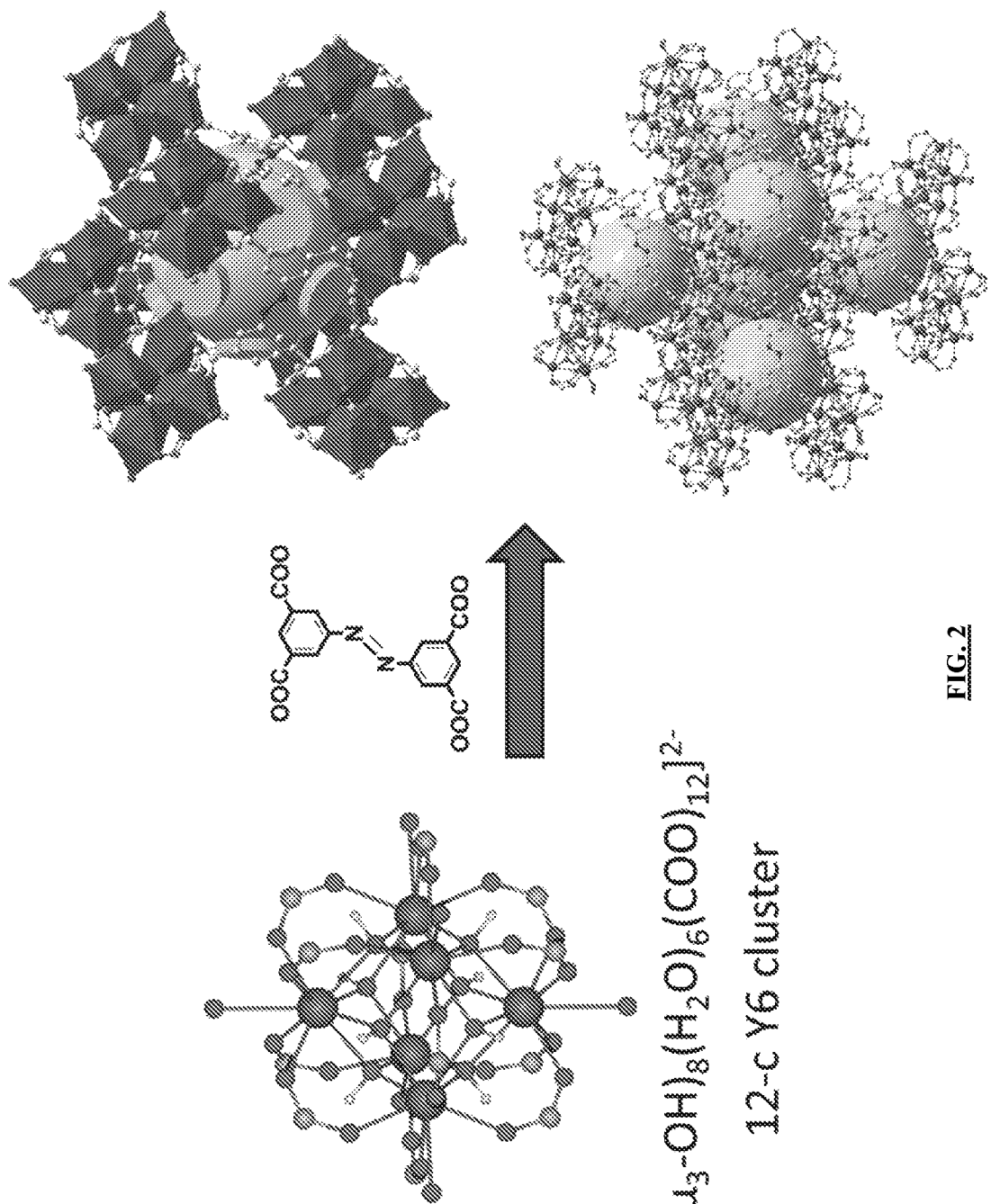
FIG. 2 illustrates a crystal structure of Y-abtc. Y-abtc is built on 12-connected hexanuclear SBU, forming cage-like pores interconnected by small windows.
Figure 10:
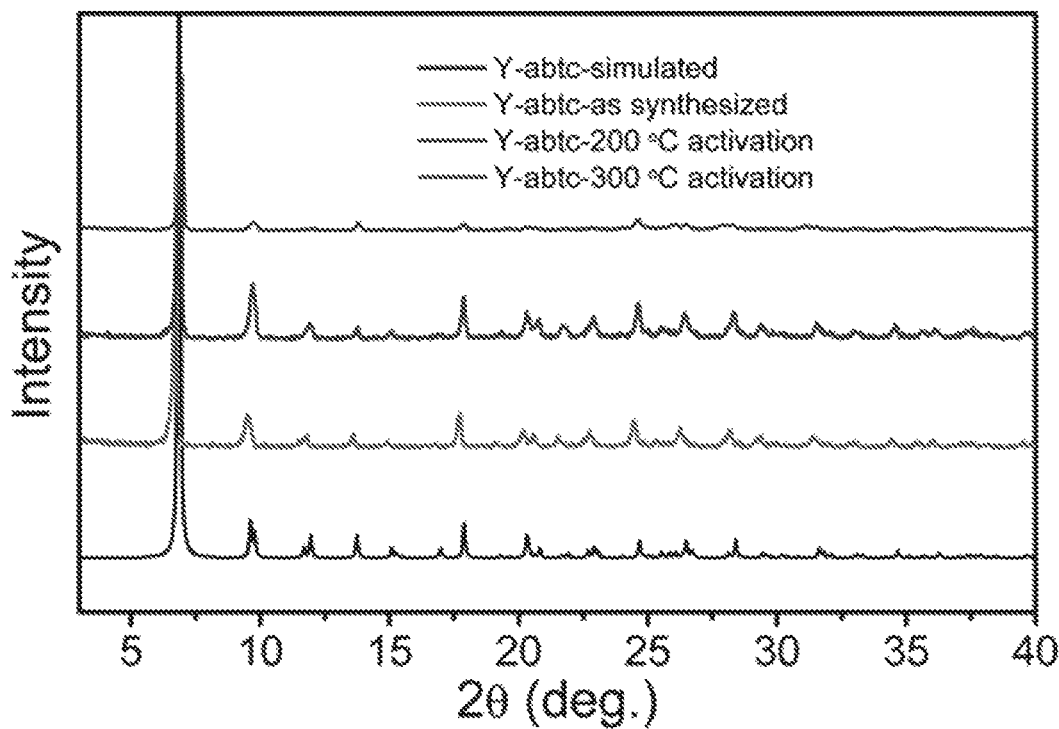
FIG. 10 illustrates a PXRD pattern for Y-abtc.
Figure 14:
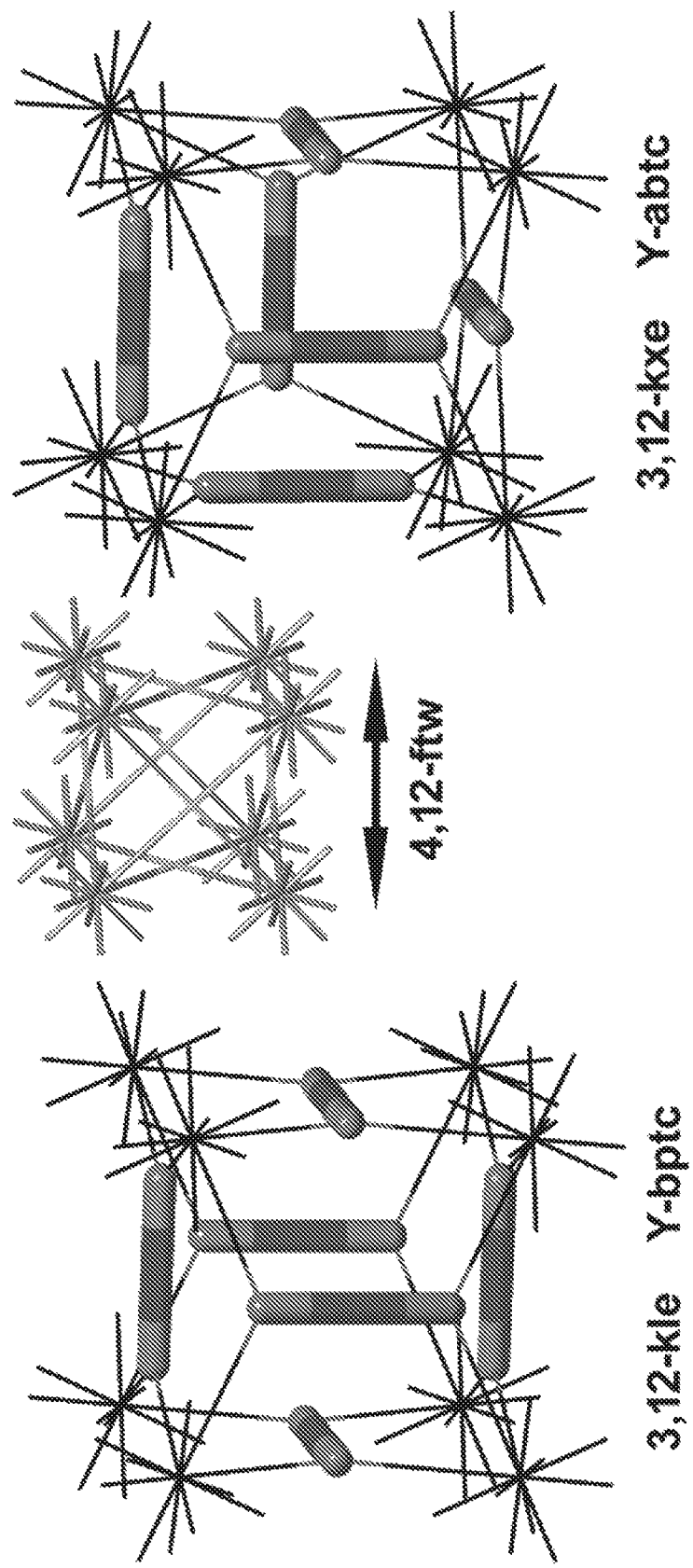
FIG. 14 illustrates a scheme comparing 3,12-kle and 3,12-kxe nets drived from 4,12-ftw.

The pore size of Y-bptc was effectively reduced with respect to Zr-bptc as a result of topology-directed SBU replacement. Such reduction was found to be overdone, making the pore window too small to adsorb either propane or propylene. Thus further tuning of the pore size was conducted by using a slightly longer organic ligand 3,3',5,5'-azobenzene-tetracarboxylate ($H_4$abtc) with the Y6 SBU. Solvothermal reactions of $Y(NO_3)_3 \cdot 6H_2O$ and $H_4$abtc under conditions similar to that of Y-bptc yielded light-yellow, small, block-shaped crystals (FIG. 7B). Although powder X-ray diffraction patterns indicate its high crystallinity (FIG. 10), attempts at determining the structure by single crystal X-ray diffraction analysis were unsuccessful. The crystal structure was instead determined through ab initio structure solution methods (see Ab initio structure solution from powder XRD data). Indexing of the powder pattern suggested that Y-abtc, differently from Y-bptc, crystallized in a rhombohedral rather than a cubic space group. This was eventually confirmed by a successful structure solution ($R_p$, $R_{wp}$ and $R_{Bragg}$=0.0754, 0.1022 and 2.218, respectively, FIG. 11) in the R-3c space group. The overall connectivity of Y-abtc was identical to that of Y-bptc (FIG. 2). However, the cages were no longer cubic, because of the rotation of the octahedron driven by the connectivity of the different ligands (FIGS. 12A-12D). As a result, for each face of the cube in Y-bptc, the plane described by the 4 centers of mass of the octahedrons and the one described by the ligand are coincident. For Y-abtc, however, the two planes are not coincident. Without intending to be limited to any particular theory, this is likely due to 1) the mutual rotation of the octahedrons and 2) the coordination geometry of the ligand. The ligand coordination is straight on the Y atom for two COO$^-$ groups and above and below from this plane by the other two COO$^-$ groups (FIG. 13A-13E). This gives rise to the contraction and distortion of the cage. Y-abtc adopted a 4,12-c connectivity, which is different from Zr-abtc with 4,8-c connectivity, as a result of the larger aspect ratio of abtc$^{4-}$ (FIGS. 1A-1B). In the commonly used description ("single node" deconstruction) the SBU is a 12-coordinated node and the ligand 4-c (regardless of the shape) resulting in the 4,12-c ftw underlying net. Using the "all node" deconstruction (called "cluster" in ToposPro) the tetratopic ligand is described as formed by two 3-c nodes. This allows for the consideration of the shape and orientation of the ligand on the underlying net giving three 3,12-c nets derived from 4,12-ftw: ttv, kle and kxe. Until recently only 3,12-kle was observed for ligands of rectangular shape and symmetry $D_{2h}$. Y-bptc now also falls within this category. The change of the ligand to abtc (lowering the symmetry to $C_{2h}$) in Y-abtc gave access to the new topology 3,12-kxe that differs from 3,12-kle in the relative orientations of the ligands as shown in the FIG. 14. The analogous Tb-abtc structure was also determined and comparison between the Tb-abtc and Y-abtc confirmed the ab initio structure solution from powder diffraction data because the two structural models strongly agreed. The syntheses of Y-bptc and Y-abtc could be scaled up with well retained crystallinity (FIGS. 12A-12D and 13A-13E).

Example 2: Characterization and Hydrocarbon Separation

Figure 15A:
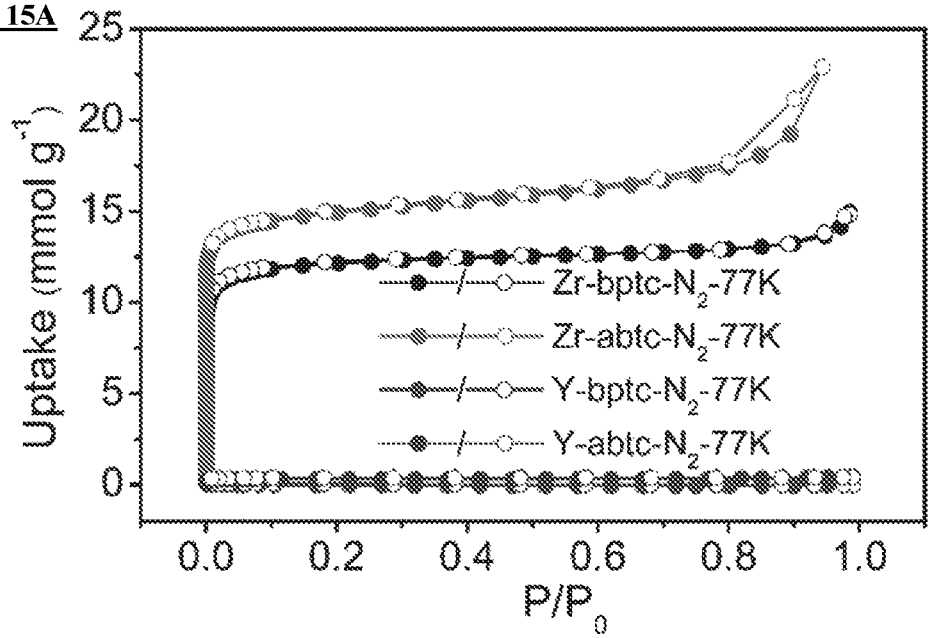
FIG. 15A illustrates a graph showing $N_2$ adsorption-desorption isotherms of Zr-bptc, Zr-abtc, Y-bptc and Y-abtc at 77 K.
Figure 15B:
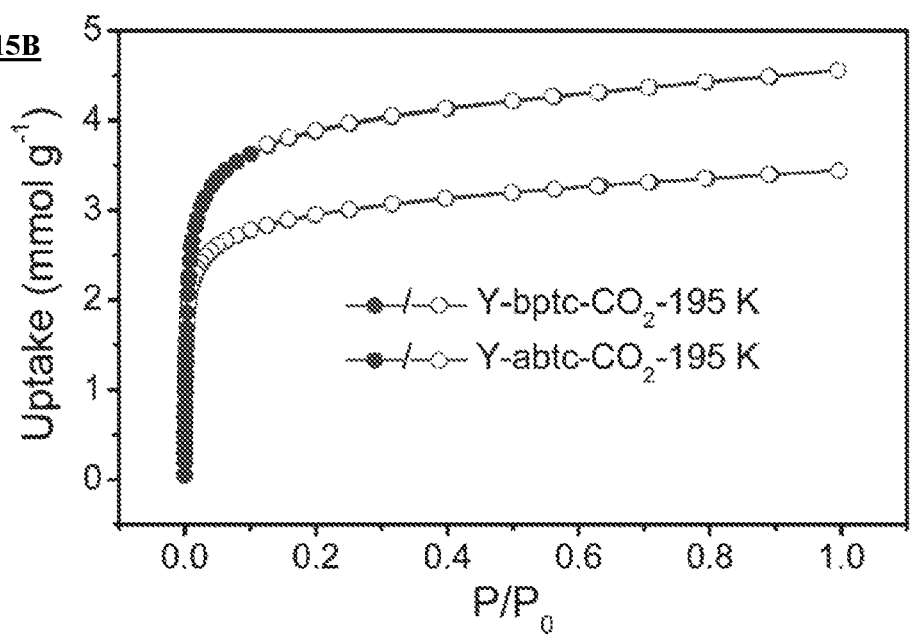
FIG. 15B illustrates a group showing $CO_2$ adsorption-desorption isotherm of Y-bptc and Y-abtc at 195 K.

Porosity characterization by $N_2$ adsorption at 77 K was unsuccessful for Y-bptc and Y-abtc as neither of them showed noticeable uptake of $N_2$ (FIGS. 15A-15B). This is different from their Zr-based analogues (Zr-bptc and Zr-abtc) which adsorbed substantial amount of $N_2$ at 77 K. Without intending to be limited to any particular theory, a possible reason could be the existence of balancing cations in the Y-based structures, leading to the suppression of accessible pores which does not allow for the diffusion of $N_2$ into the pores at cryogenic temperature. Porosity was instead characterized by $CO_2$ adsorption at 195 K. Y-bptc and Y-abtc both exhibited Type I adsorption profile for $CO_2$, with saturation capacities of 3.2 and 3.7 mmol g$^{-1}$, respectively. The estimated surface areas and pore volumes were 319 and 427 m$^2$ g$^{-1}$, and 0.14 and 0.18 cc g$^{-1}$ for Y-bptc and Y-abtc, respectively. These values are noticeably lower than their Zr-based analogues.

Figure 3A:
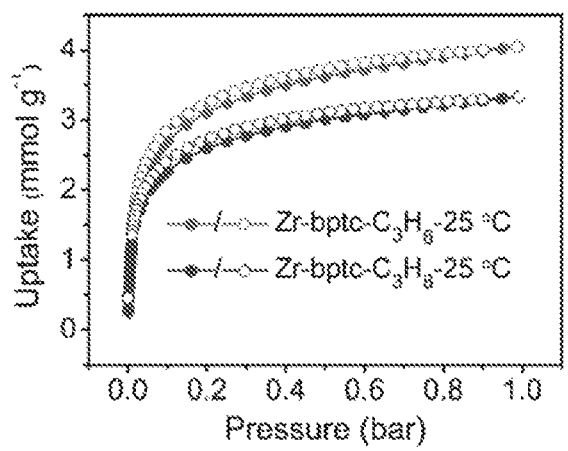
FIGS. 3A-3D illustrate graphs showing single-component adsorption isotherms of propane and propylene at 25° C. for Zr-bptc (FIG. 3A), Zr-abtc (FIG. 3B), Y-bptc (FIG. 3C), and Y-abtc (FIG. 3D).
Figure 3B:
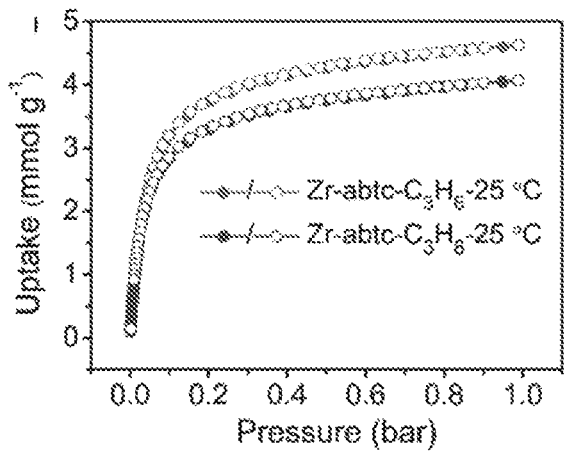
Figure 3C:
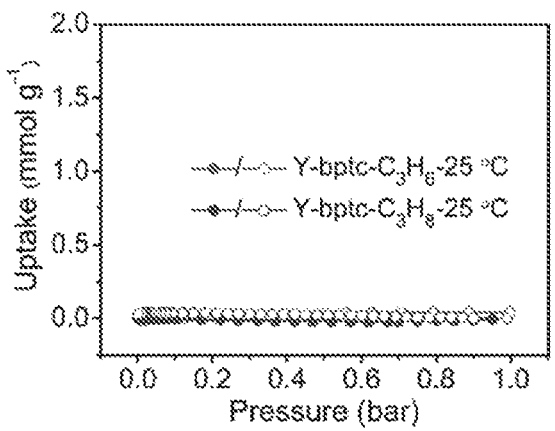

Adsorption isotherms of propane and propylene on Zr-bptc and Zr-abtc at room temperature indicate neither of them is capable of discriminating the two gases (FIGS. 3A-3B). The adsorption capacity of propane and propylene are similar for both compounds. No diffusional restriction has been observed. The results suggest that the pore sizes of Zr-bptc and Zr-abtc are too large for the separation of propane and propylene. In contrast, while Y-bptc features the same connectivity and topology as Zr-bptc, it adsorbs neither propane nor propylene, indicating its pore size is smaller than that of Zr-bptc (FIG. 3C). Without intending to be limited to any particular theory, this could be attributed to the existence of the balancing cation, dimethylammonium, which might block the entrance of the cage and suppress the effective pore aperture.

Figure 3D:
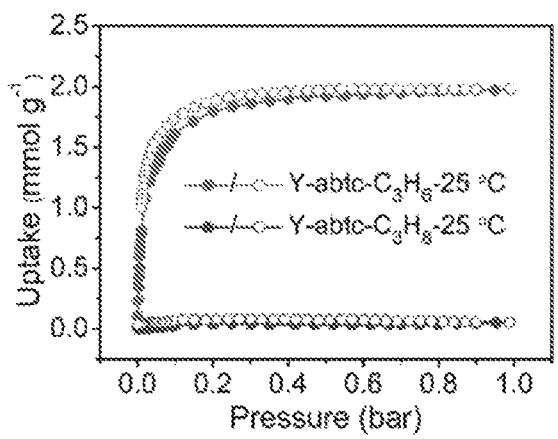
Figure 3E:
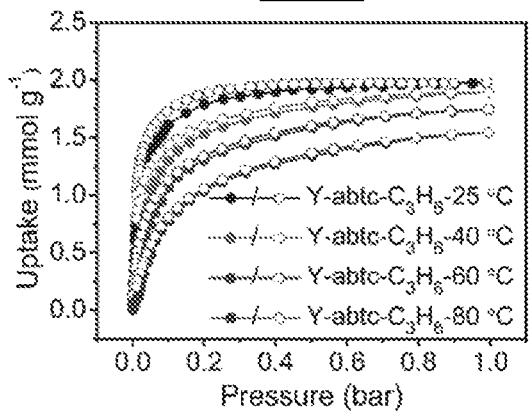
FIG. 3E illustrates a graph showing propylene adsorption isotherms for Y-abtc at 25, 40, 60, and 80° C.
Figure 3F:
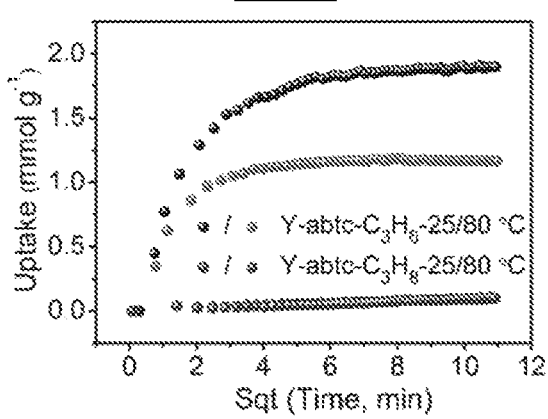
FIG. 3F illustrates a graph showing adsorption rates of propane and propylene on Y-abtc at 25 and 80° C., with a partial pressure of 0.8 bar.

Unlike Y-bptc, Y-abtc adsorbed appreciable amounts of propylene at room temperature, with an uptake capacity of ~2 mmol g$^{-1}$ at 1 bar (FIG. 3D). The adsorption was fully reversible and features a Type I profile. Adsorption isotherms at higher temperatures (40, 60, 80° C.) have also been collected, and at 80° C. propylene adsorption capacity is ~1.5 mmol g$^{-1}$ (FIG. 3E). Adsorption strength was evaluated by isosteric heat of adsorption ($Q_{st}$), calculated by adsorption isotherms at 40, 60, and 80° C. and a $Q_{st}$ value of ~50 kJ mol$^{-1}$ was obtained. This value is comparable to M$_2$(dobdc) (M=Mg, Mn, Fe, Co, Ni, Zn), but slightly lower than that of KAUST-7 (57.4 kJ mol$^{-1}$) (Cadiau, et at, *Science* 2016, 353, 137; Geier, et al., *Chemical Science* 2013, 4, 2054). In contrast, adsorption isotherms at room temperature showed essentially no uptake of propane on Y-abtc, suggesting a size-exclusion behavior. To confirm that the discrimination toward propane and propylene by Y-abtc is through selective size exclusion rather than kinetic separation and to assess the adsorption kinetics of propylene, adsorption rates of propane and propylene at 25° C. and 80° C. were measured with a gravimetric adsorption analyzer. As shown in FIG. 3F, adsorption of propylene reached equilibrium within 20 and 10 minutes at 25 and 80° C., respectively, without noticeable diffusional restrictions. In contrast, negligible uptake of propane was detected and no difference was observed with respect to adsorption kinetics at 25 and 80° C. This is consistent with the adsorption isotherms, indicating propane is fully excluded from diffusing into the pore of Y-abtc. These results suggest that Y-abtc represents a rare adsorbent that exhibits selective molecular exclusion behavior for propane over propylene.

Figure 4A:
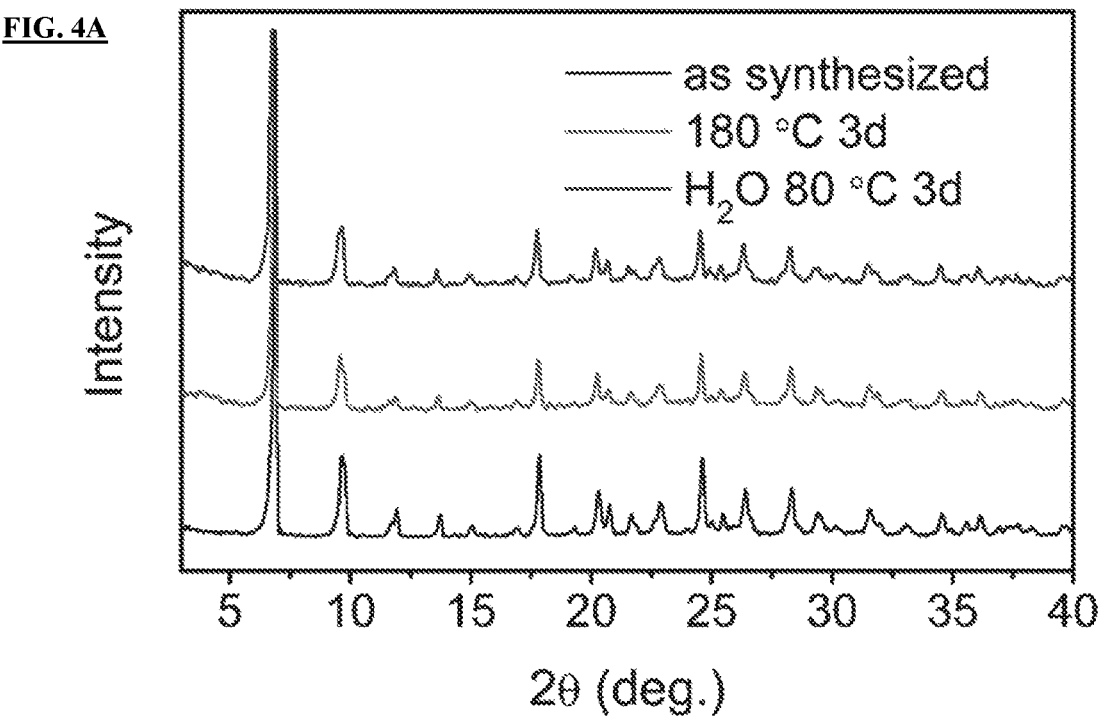
FIGS. 4A-4B illustrate graphs showing stability tests for Y-abtc.
Figure 4B:
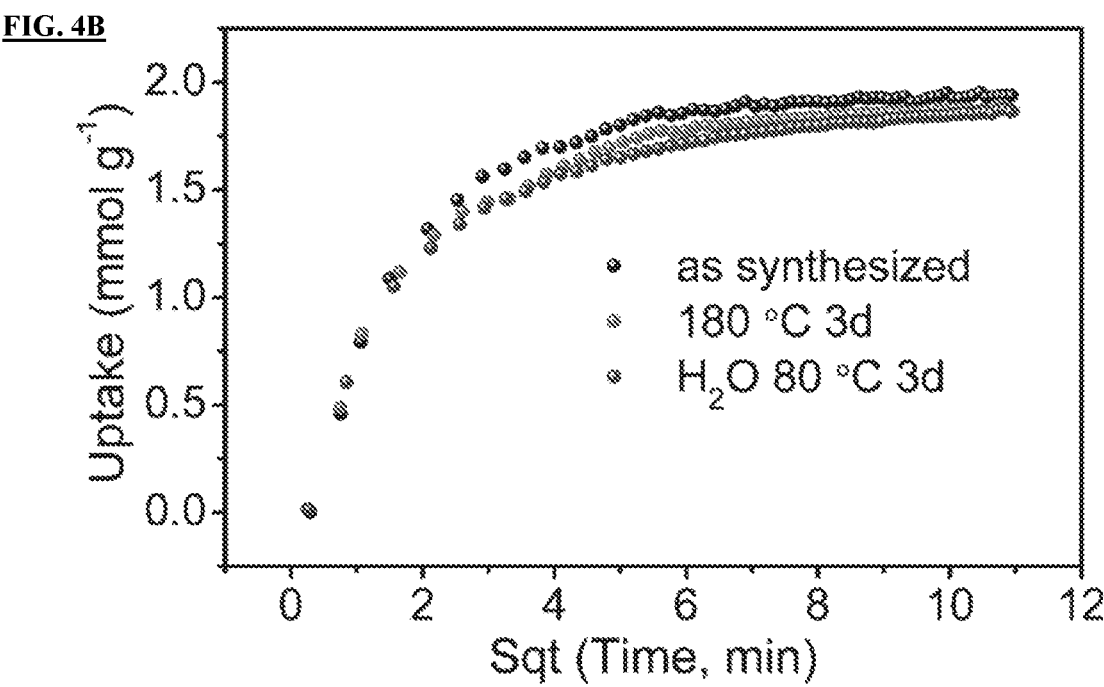
Figure 6A:
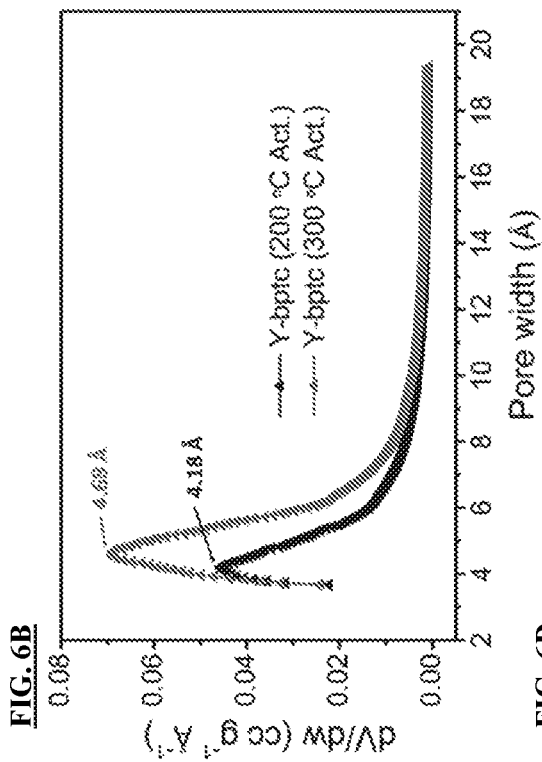
FIG. 6A-6B illustrate adsorption-desorption isotherms of $CO_2$ at 195 K on Y-bptc activated at 200 and 300° C.
Figure 6B:
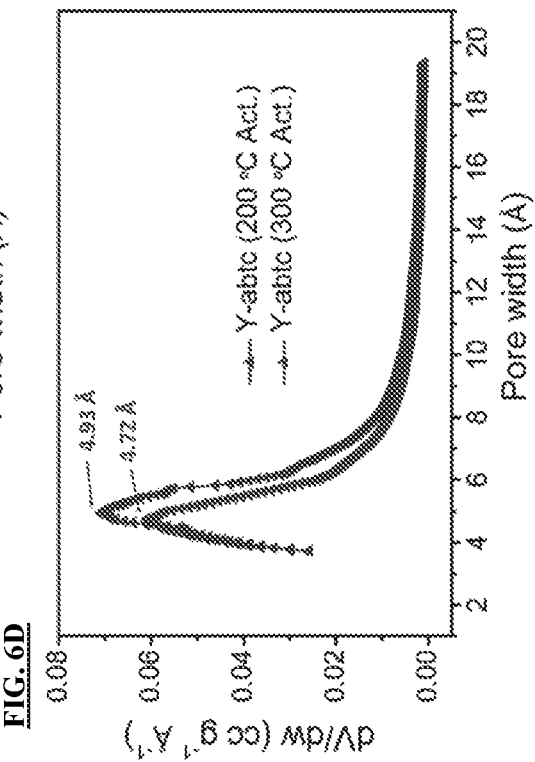
Figure 6C:
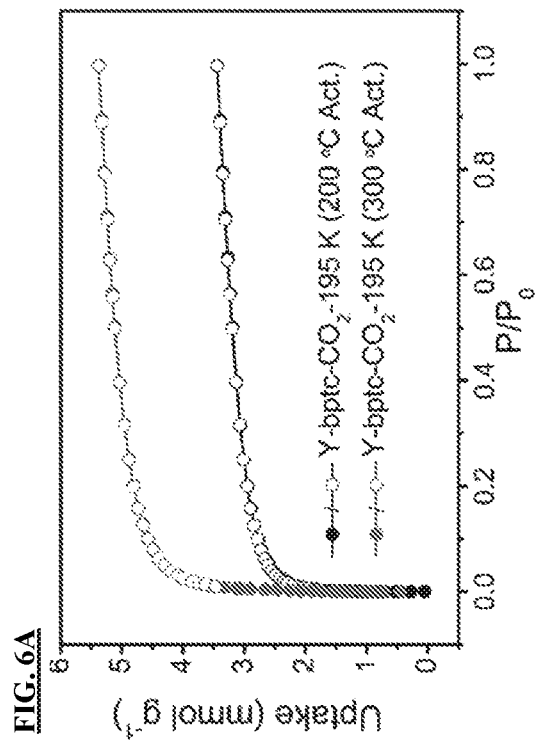
FIG. 6C-6D illustrate adsorption-desorption isotherms of $CO_2$ at 195 K on Y-abtc activated at 200 and 300° C.
Figure 6D:
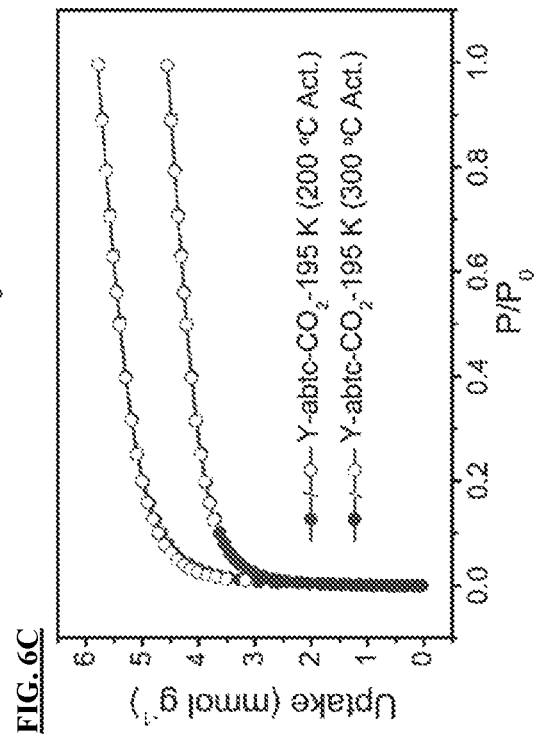

To assess the framework robustness of Y-abtc with respect to crystallinity and adsorption performance, stability tests were performed with thermal and hydrothermal treatments. In situ variable-temperature PXRD analysis showed that the framework remained intact up to 520° C., the temperature at which loss of crystallinity starts to take place (FIG. 16). Le Bail refinement and parametric treatment of the VT-PXRD data along the whole range of temperature (RT—540° C.) showed that during activation the framework underwent a slight contraction of the unit cell volume of less than 1% (FIG. 17). This result suggests that Y-abtc possesses high framework robustness, similar to its Zr-based analogues (Zr-bptc and Zr-abtc). As shown in FIG. 4A, after being heated at 180° C. in open air or in water at 80° C. for 3 days, the crystallinity of Y-abtc was well maintained, as evidenced by the PXRD patterns collected on the samples after treatments. More importantly, their propylene adsorption capacity was also fully retained (FIG. 4B).

Figure 18A:
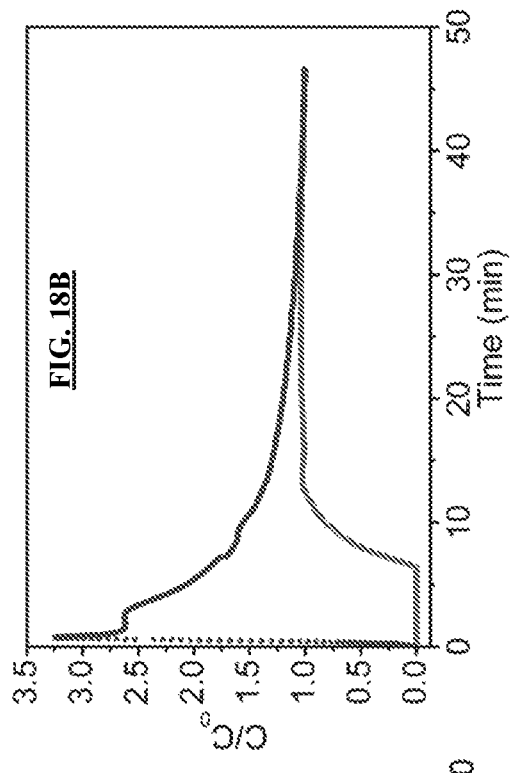
FIGS. 18A-18D illustrate a set of graphs of breakthrough curves for binary mixtures of propane and propylene for propane: propylene=50:50 (total flow rate: 1.6 cc $min^{-1}$) (FIG. 18A), propane: propylene=50:50 (total flow rate: 4 cc $min^{-1}$) (FIG. 18B), propane: propylene=10:90 (total flow rate: 1.6 cc $min^{-1}$) (FIG. 18C), propane: propylene=5:95 (total flow rate: 1.6 cc $min^{-1}$) (FIG. 18D).
Figure 18B:
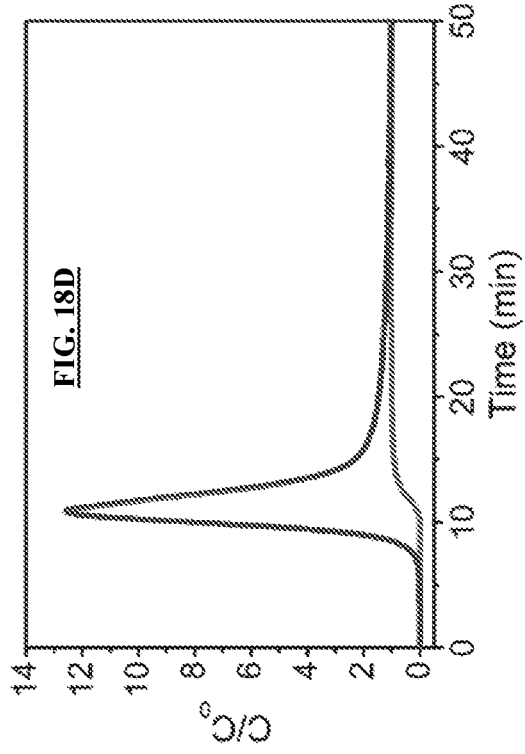
Figure 19:
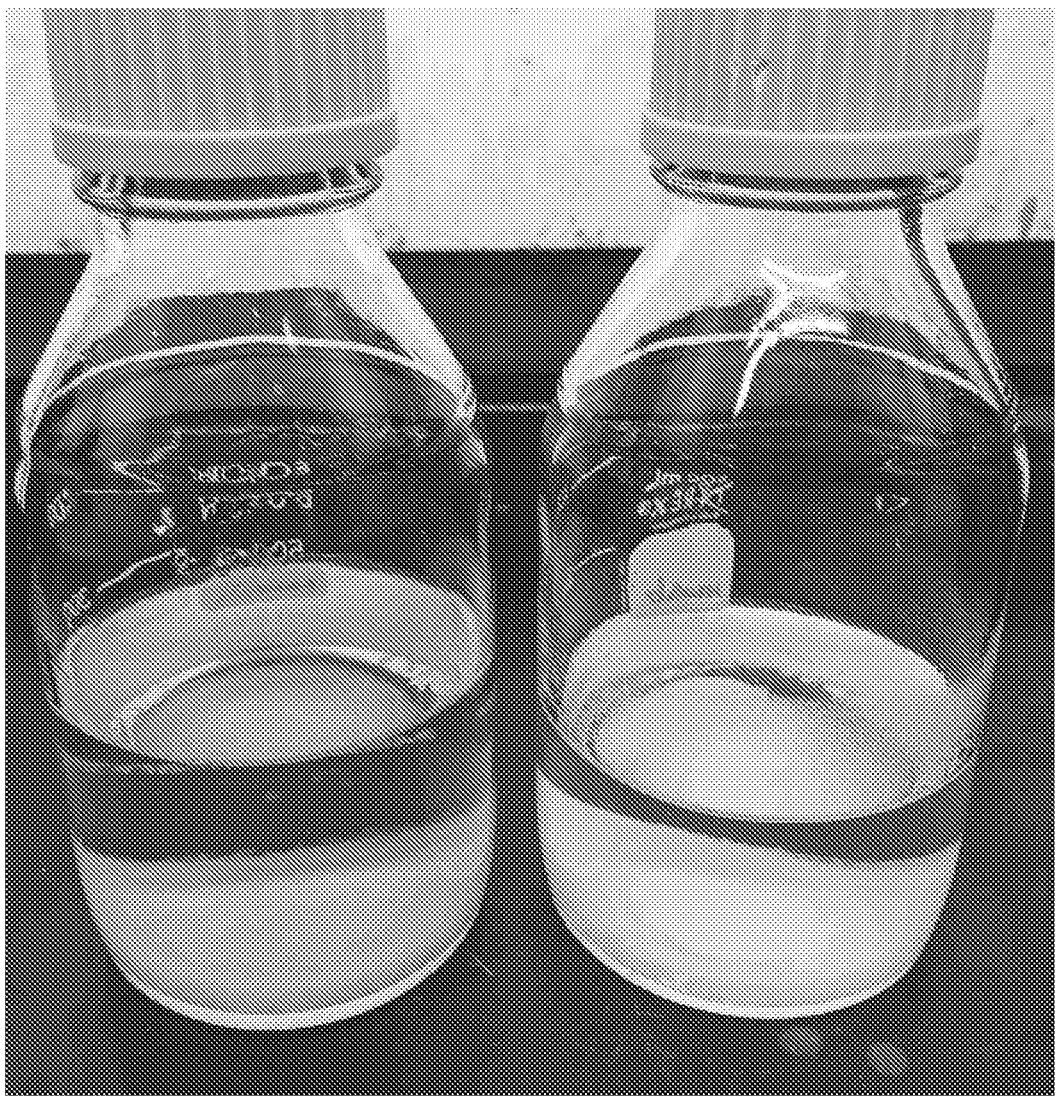
FIG. 19 illustrates a photograph of gram scale synthesis of Y-abtc (left) and Y-bptc (right).
Figure 21:
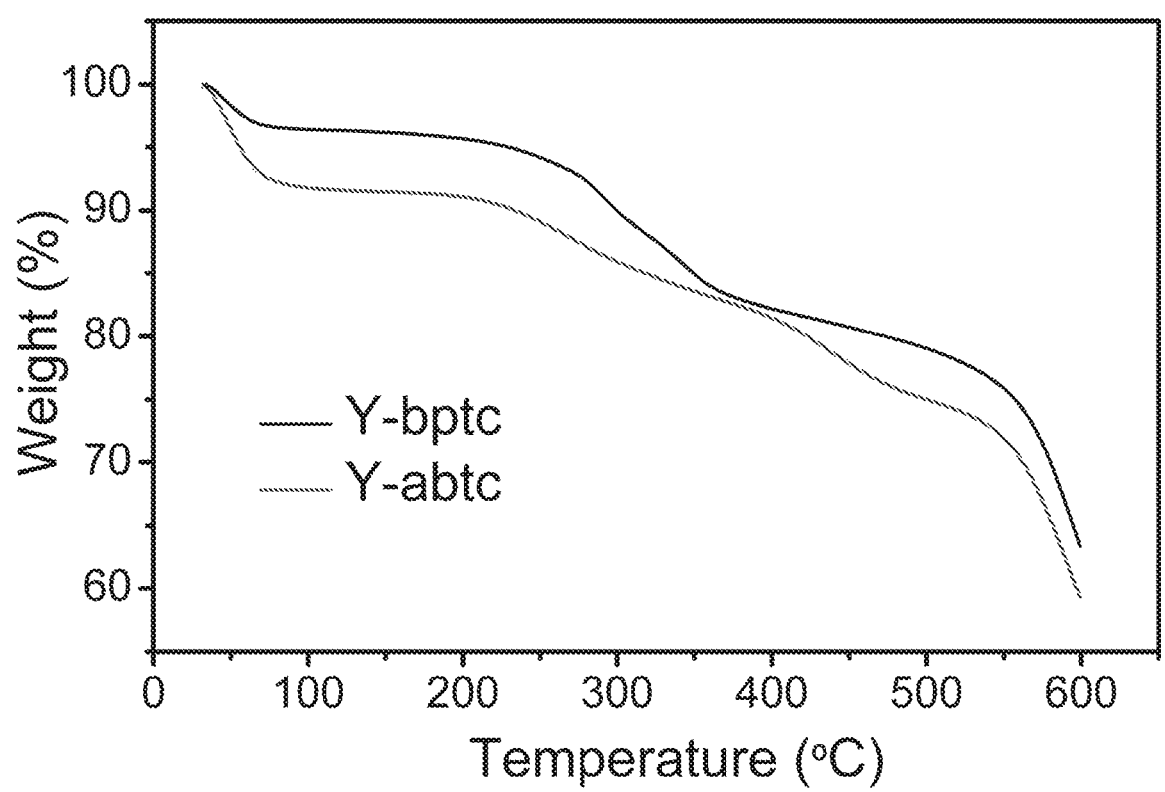
FIG. 21 illustrates a set of TGA curves for Y-bptc and Y-abtc.

As suggested by the single component adsorption results, Y-abtc exhibited the potential for separating propane and propylene through complete sieving. Multicomponent column breakthrough experiments were performed at room temperature to assess the separation capability under mixed gases conditions. An equimolar binary mixture of propane and propylene was introduced to a column at a total flow rate of 1.6 ml min$^{-1}$ as a feed. The breakthrough curve revealed that propane breaks at the very first minute indicating that no noticeable retention took place in the column (FIG. 5A). This is consistent with the single component adsorption result that Y-abtc does not adsorb propane at room temperature. Conversely, propylene, the other component in the mixture did not elute out until the 12$^{th}$ minute, equivalent to a dynamic uptake of 1.26 mmol g$^{-1}$. This again, coincides with the pure component adsorption results that propylene can freely diffuse into the pores of Y-abtc. Subsequent desorption of the gas retained in the column by heating under helium flow yielded a propylene purity of 97.6% in the eluted gas (FIG. 5B). A following breakthrough experiment with an increased flow rate (total flow rate: 4 ml min$^{-1}$) confirmed the complete separation capability of Y-abtc was fully retained with a retention time of 12.9 minutes per gram of adsorbent for propylene (FIGS. 18A-18B), a value noticeably higher than that of KAUST-7, the MOF material with the best performance reported so far for propane/propylene separation, which has a retention time of 5.7 minutes per gram of adsorbent under the same condition (Cadiau, et al., *Science* 2016, 353, 137). This suggests that the dynamic adsorption capacity of Y-abtc for propylene is more than twice that of KAUST-7. This is a significant improvement, especially considering it is capable of complete propane/propylene separation and scalable synthesis (FIGS. 19, 20A-20B) and high stability.

Figure 18C:
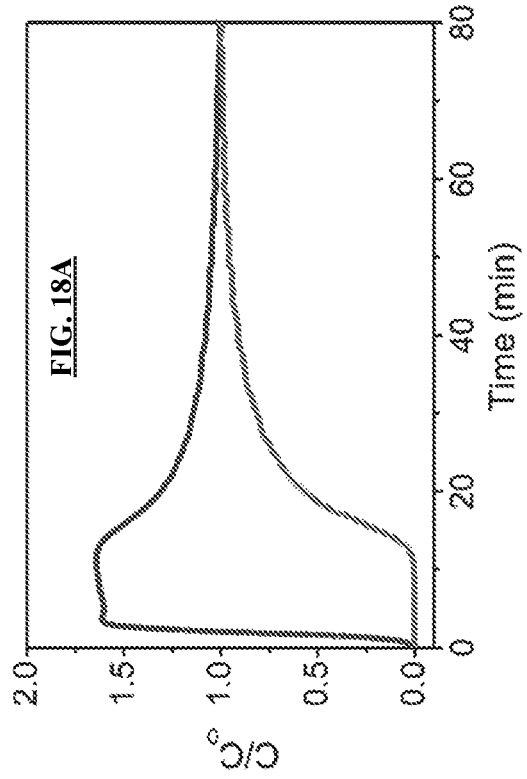
Figure 18D:
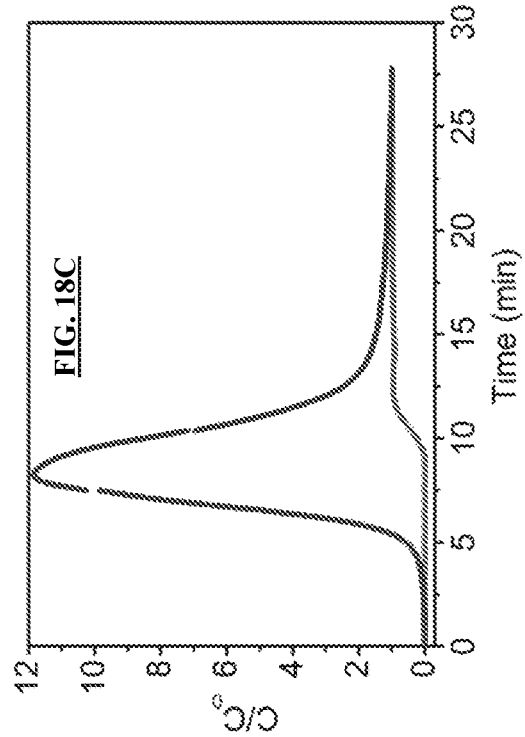

Further breakthrough experiments were performed with different propane/propylene starting ratios, i.e. propane: propylene=10:90, and propane:propylene=5:95 (FIGS. 18C-18D). Clear separation of propane and propylene with propane breaking first was observed in the breakthrough curves for both feed ratios despite the increase of the concentration of propylene in the mixture. For the measurement starting with a mixture of propane: propylene=5:95, although propane was also retained in the column for several minutes before breaking due to its low concentration, the amount adsorbed in the Y-abtc (~2 mg g$^{-1}$) was negligible (FIG. 5C). Noticeably, 99.5% pure propylene was recovered during the desorption step, a purity that well meets the requirements for the production of polymers (FIG. 5D). This result confirms that Y-abtc, as an adsorbent for complete sieving of propane from propylene, is capable of producing polymer-grade propylene by adsorptive separation method.

Figure 22A:
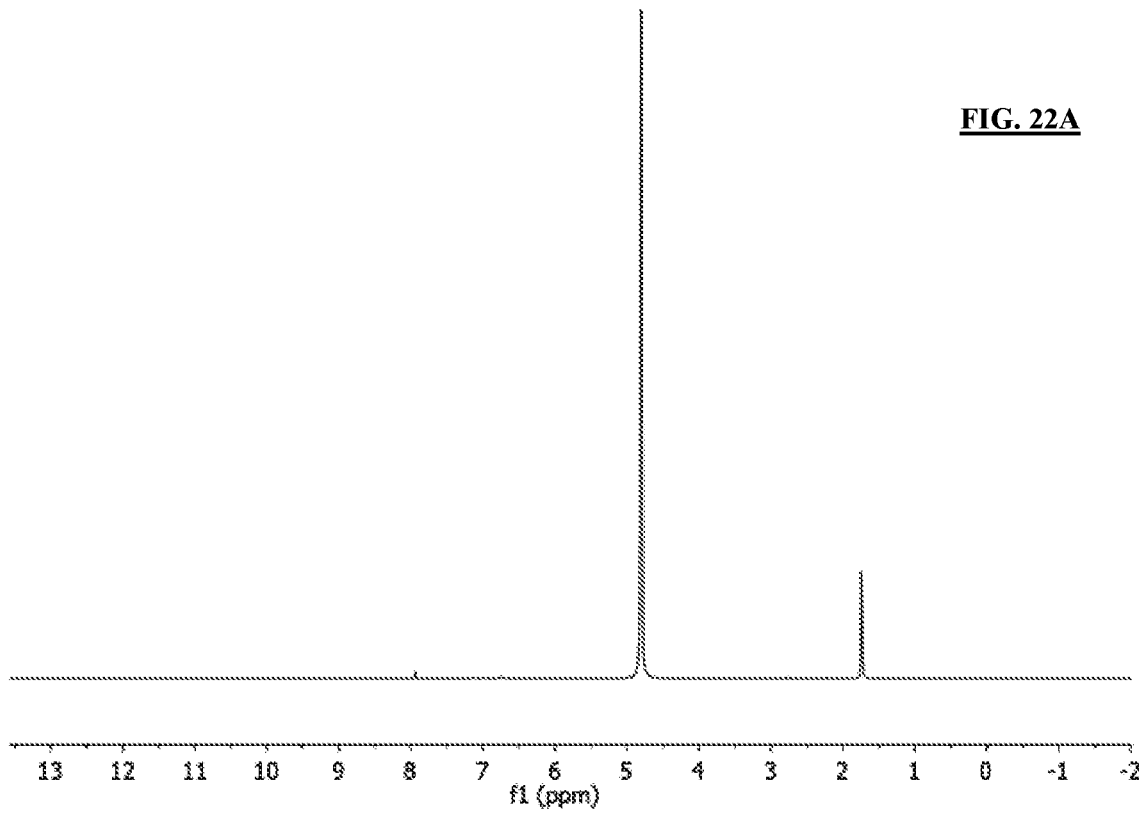
FIGS. 22A-22B illustrate NMR spectra of base digested Y-abtc activated at 200° C.
Figure 22B:
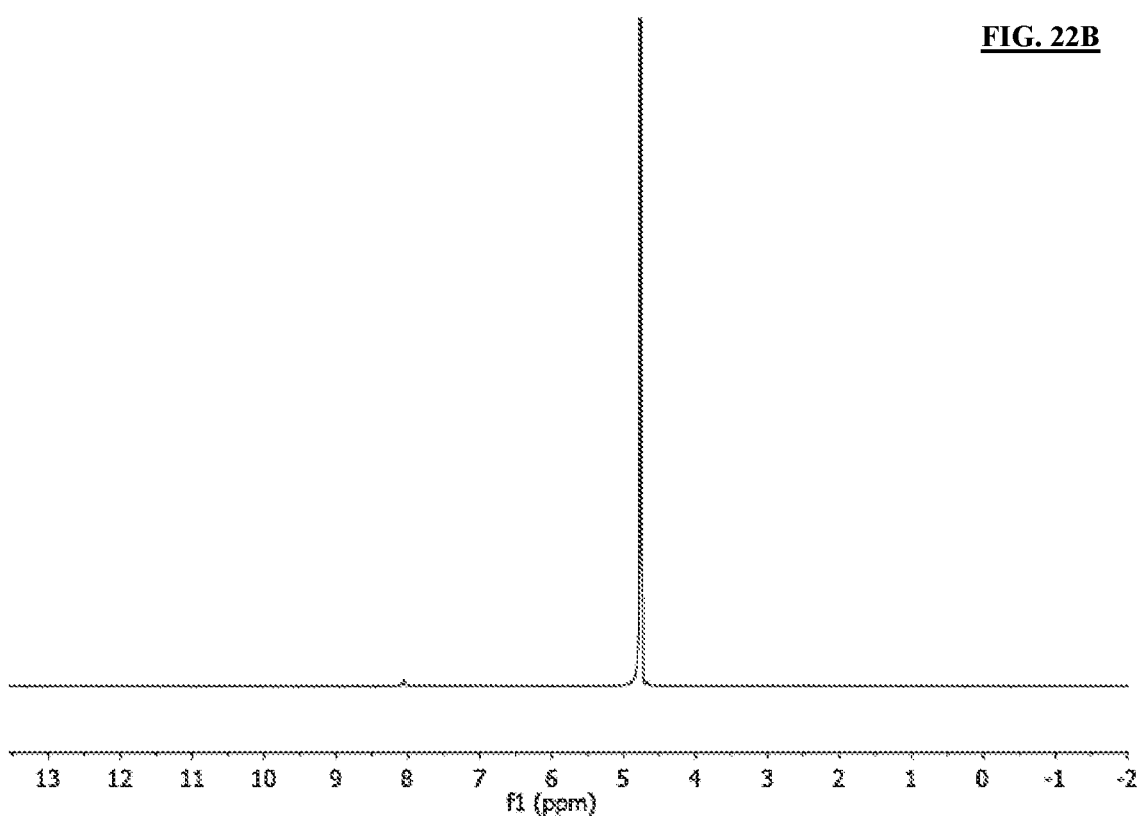
Figure 23A:
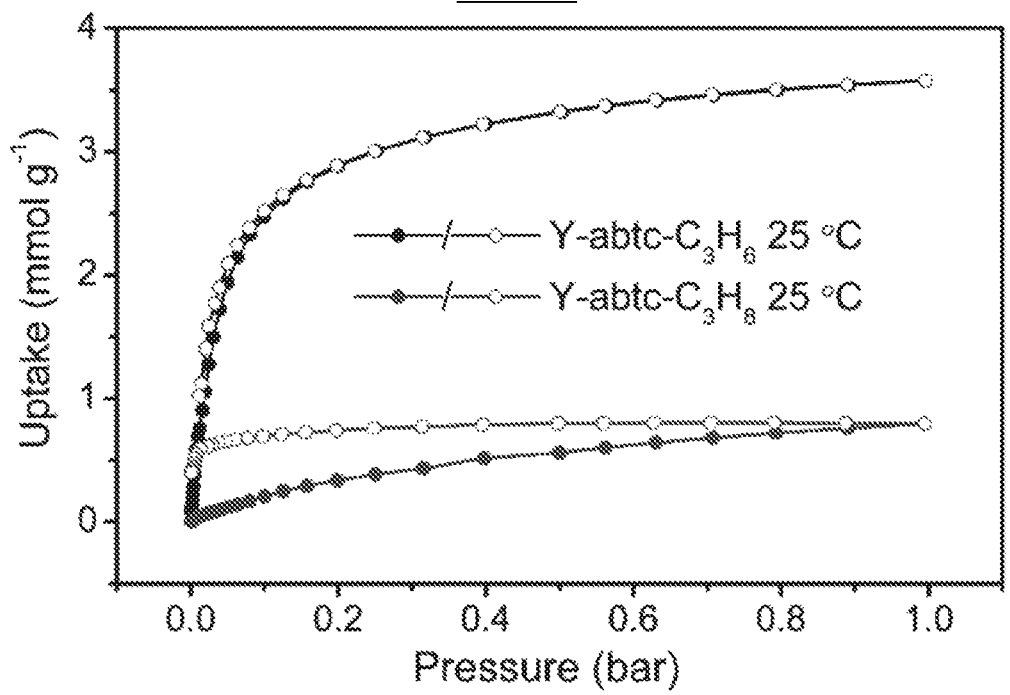
FIGS. 23A-23B illustrate graphs showing adsorption isotherms (FIG. 23A) and adsorption rates (FIG. 23B) at 25 and 80° C. for Y-abtc activated at 300° C.
Figure 23B:
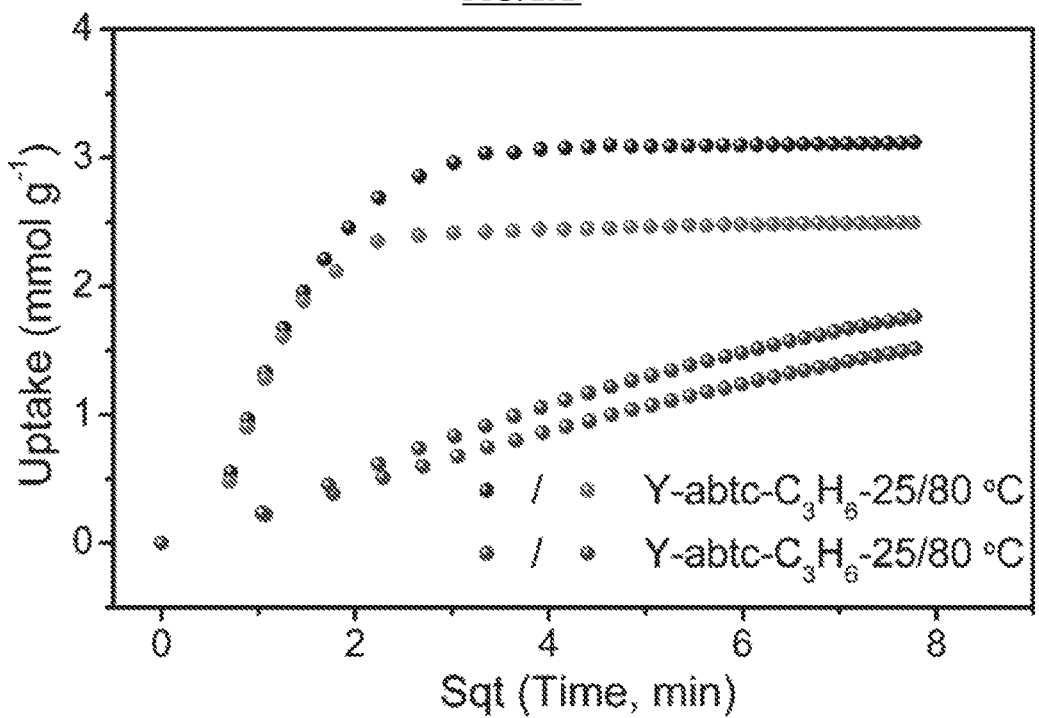
Figure 24:
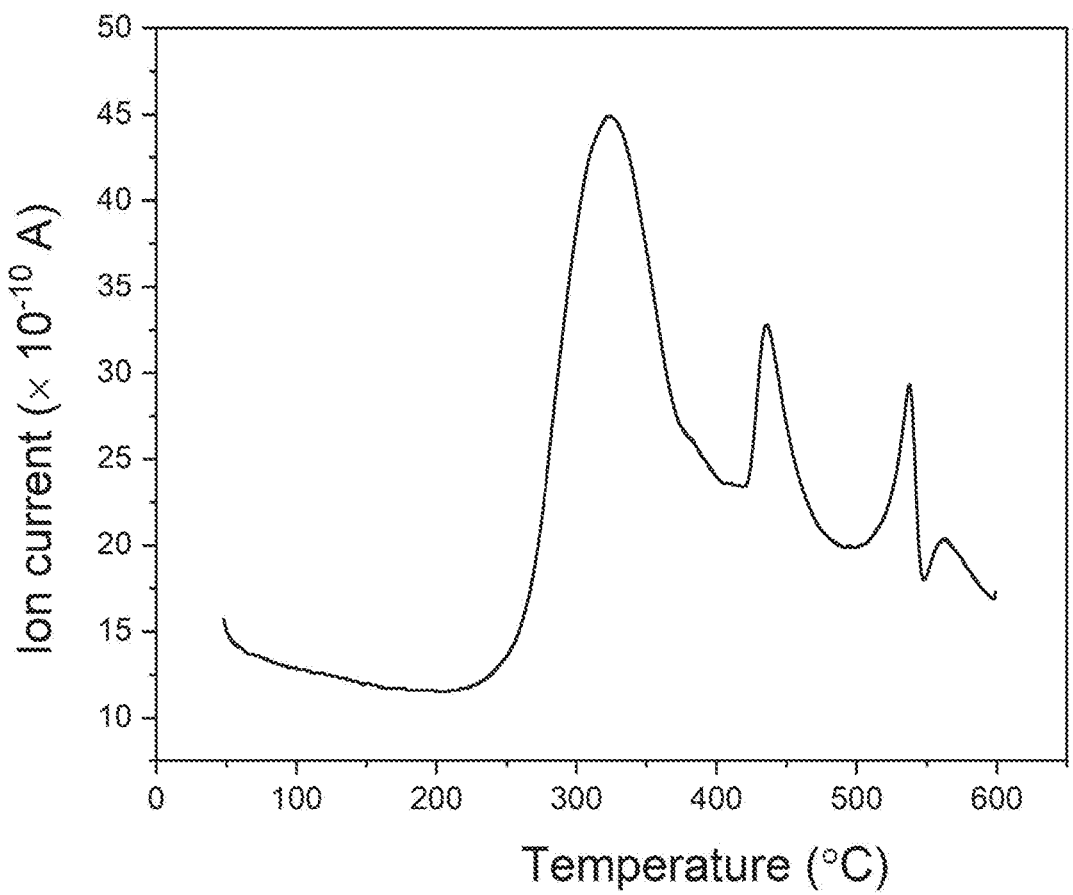
FIG. 24 illustrates a TG-MS spectrum for m=45.

The 4,12-c Y-abtc/Y-bptc are similar to their Zr-based analogue Zr-bptc with respect to overall connectivity and pore structure. However, the subtle difference in their structures lead to their distinct adsorption behaviors. One noticeable difference between them is that the framework of the Y-MOFs are anionic while the Zr-MOFs are neutral. To evaluate how the balancing cations in Y-MOFs may influence their pore apertures and contribute to their adsorption properties, gas adsorption measurements were performed on Y-abtc samples activated at different temperatures. The aforementioned adsorption measurements were performed on Y-abtc activated at 200° C. (FIG. S21). $^1$H NMR spectrum of the digested MOF sample indicated the existence of dimethylammonium in the activated compound (FIG. 22A). Y-abtc activated at 300° C. showed enhanced adsorption capacity and kinetics toward propylene, compared to that of the sample activated at 200° C. (FIGS. 23A-23B), with adsorbed propylene of 3.5 mmol g$^{-1}$ (v.s. 2.0 mmol g$^{-1}$ if activated at 200° C.) at 25° C. and 1 bar. Adsorption rate measurements showed the adsorption of propylene reached equilibrium within 10 and 4 minutes at 25 and 80° C., respectively. Upon activation at 300° C., Y-abtc adsorbed a substantial amount of propane, though the diffusion rate was relatively slow. These results suggest that the increased activation temperature noticeably enlarged the pore apertures of Y-abtc. To support this hypothesis, CO$_2$ adsorption experiments at 195 K were carried out on Y-abtc samples activated at 200 and 300° C. The sample activated at 300° C. adsorbed more CO$_2$ under saturation (FIGS. 6A-6D). Pore size distribution analysis confirmed the enlarged pore size (4.93 Å) compared to that of the sample activated at 200° C. (4.72 Å). The peak associated with dimethylammonium disappeared in the ¹H NMR spectrum of the sample activated at 300° C. (FIG. 22B), indicating the decomposition of the organic cation. TG-MS measurements indicated that upon heating to 300° C. the material released a molecule with a molecular mass of 45, which can be attributed to dimethylamine. This suggests the decomposition of a dimethylammonium cation resulting in the formation of dimethylamine, leaving behind a proton acting as balancing cation. Without intending to be limited to any particular theory, this can explain the observed enlarged pore aperture and its adsorption behavior toward propylene and propane. $CO_2$ adsorption results and pore size distribution analysis on Y-bptc suggested a similar trend. This is interesting and noteworthy as ionic MOF frameworks are quite common and making use of the balancing ionic species as a pore size regulator can potentially be an effective way to develop adsorbents with optimal adsorption/separation performance.

Example 3

Figure 25:
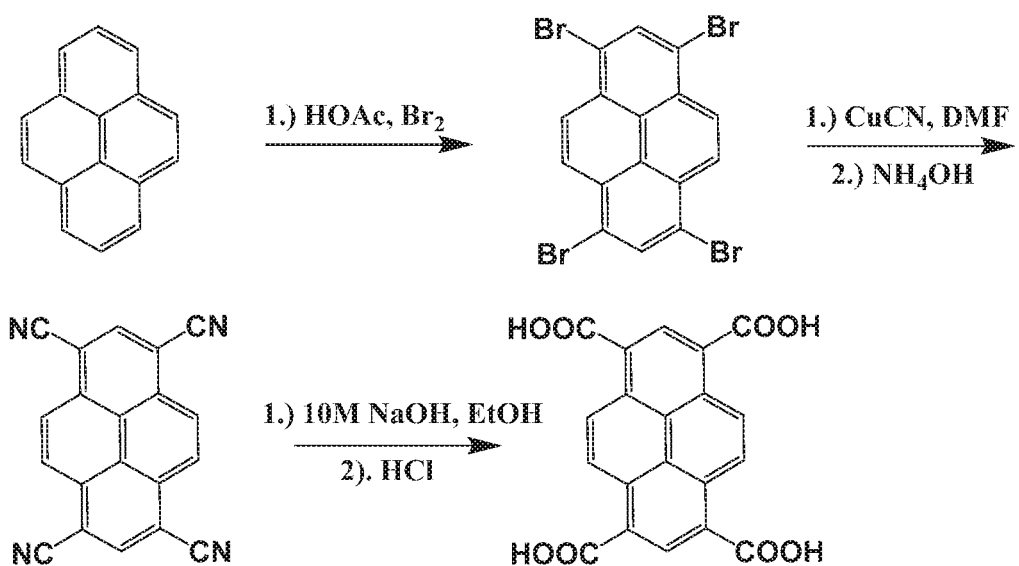
FIG. 25 illustrates an exemplary synthesis of H₄ptca.

Ligand pyrene-1,3,6,8-tetracarboxylic acid ($H_4$ptca) was synthesized in a total of 3 steps (FIG. 25). The first step was the bromination of pyrene to produce tetrabromopyrene. Tetrabromopyrene then underwent a cyanation reaction to produce tetracyanopyrene. Lastly, hydrolysis of the four nitrile group with NaOH and acidification led to the final product. Purification was accomplished through recrystallization from DMF.

The following complexes of ($H_4$ptca) and distinct metals (M) were prepared:

(a) M-ptca (M=Zr, Hf)

$ZrOCl_2 \cdot xH_2O$ or $HfOCl_2 \cdot xH_2O$ (35.7 mg) and $H_4$ptca (16 mg) were heated in 5 mL formic acid and 5 mL DMF at 120° C. for 72 hrs.

(b) M-ptca (M=Y)

$Y(NO_3)_3 \cdot 9H_2O$ (38.3 mg) and $H_4$ptca (16 mg) were heated in 5 mL DMF, 2 mL $H_2O$, and 1.2 g 2-fluorobenzoic acid at 120° C. for 72 hrs.

Figure 26:
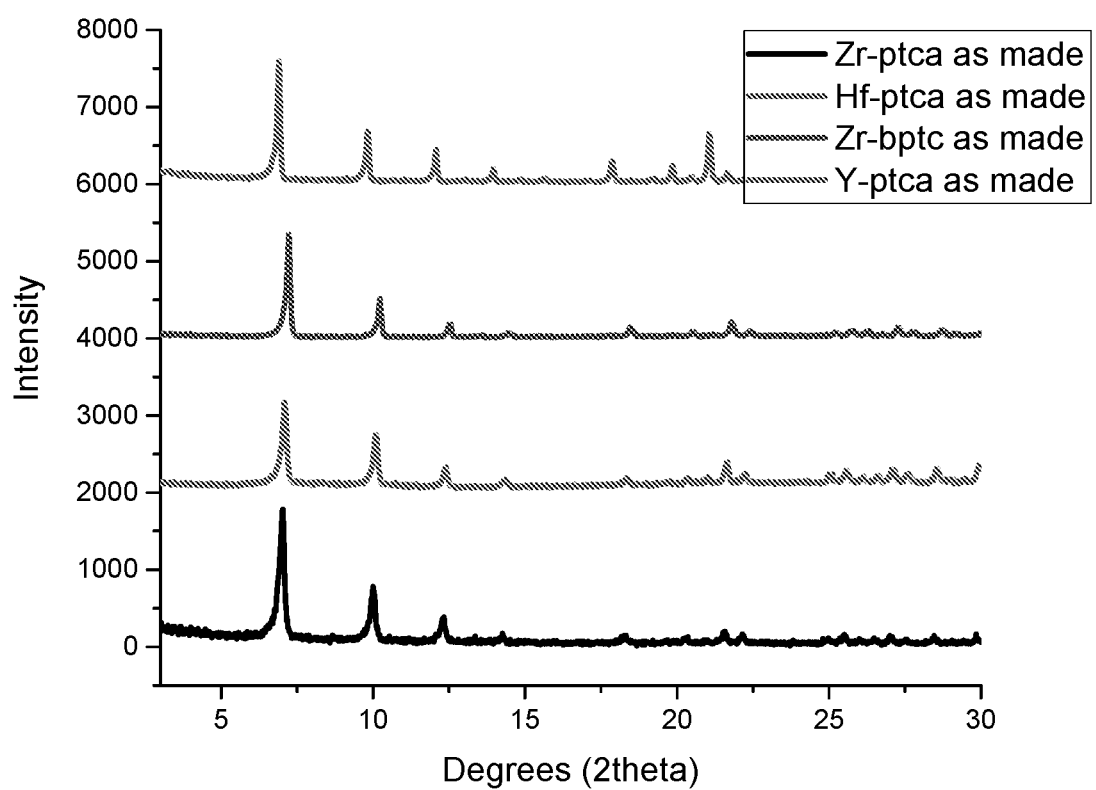
FIG. 26 illustrates PXRD patterns of Zr-ptca, Hf-ptca and Y-ptca. The PXRD of Zr-bptc is included as a reference.
Figure 27:
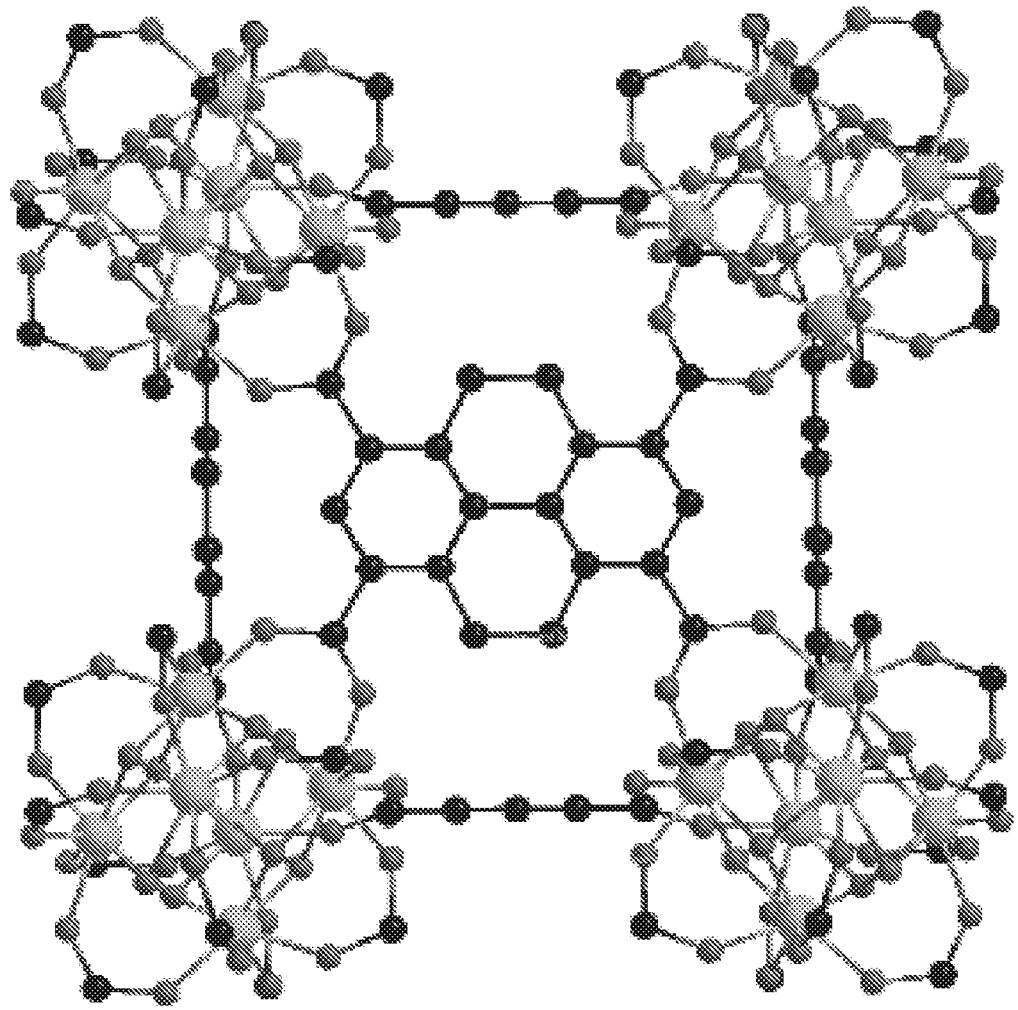
FIG. 27 illustrates the structure of M-ptca (M=Zr, Hf, Y).

The PXRD analysis of M-ptca (M=Zr, Hf, Y) shows that those complexes were isoreticular to Zr-bptc and Y-abtc, all having the same ftw topology (FIG. 26). The structure of M-ptca (M=Zr, Hf, Y) is illustrated in FIG. 27.

Enumerated Embodiments

The following exemplary embodiments are provided, the numbering of which is not to be construed as designating levels of importance.

Embodiment 1 provides a metal-organic framework comprising a metal (M) ion and a tetratopic organic ligand, wherein:

(a) the metal ion is $M^{3+}=Y^{3+}$, and the tetratopic organic ligand is

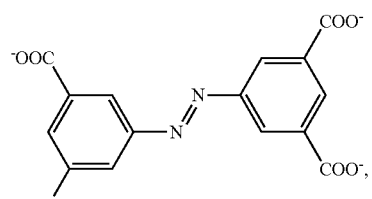

(abtc)

or (b) the metal ion is $M^{3+}=Y^{3+}$ or $M^{4+}=Zr^{4+}$ or $Hf^{4+}$, and the tetratopic organic ligand is

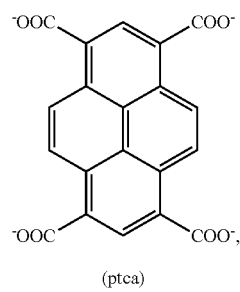

(ptca)

or (c) the metal ion is $M^{3+}=Y^{3+}$, and the tetratopic organic ligand is

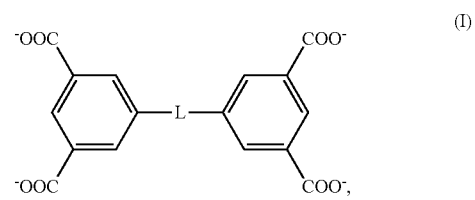

(I)

wherein L is selected from the group consisting of a bond, optionally substituted $C_1$-$C_6$ alkylene, optionally substituted $C_2$-$C_6$ alkenylene, optionally substituted $C_2$-$C_6$ alkynylene,

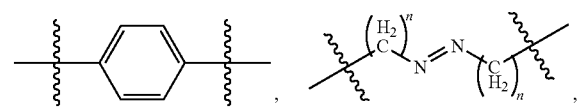

O, S, $SO_2$, NH and $NCH_3$; and each instance of n is independently an integer from 0 to 3, or (d) the metal ion is $M^{4+}=Zr^{4+}$ or $Hf^+$, and the tetratopic organic ligand is

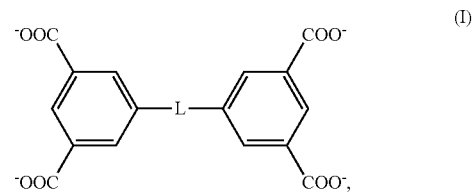

(I)

wherein L is selected from the group consisting of a bond, optionally substituted $C_1$-$C_6$ alkylene, optionally substituted $C_2$-$C_6$ alkenylene, optionally substituted $C_2$-$C_6$ alkynylene,

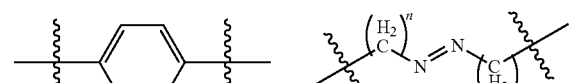

O, S, $SO_2$, NH and $NCH_3$; and each instance of n is independently an integer from 0 to 3.

Embodiment 2 provides the metal-organic framework of Embodiment 1, wherein the metal ion is in the form of a (metal ion)$_6$ cluster.

Embodiment 3 provides the metal-organic framework of Embodiment 2, wherein the (metal ion)$_6$ cluster comprises at least one selected from the group consisting of a $\mu_3$-OH bridging ligand and a $\mu_3$-O bridging ligand.

Embodiment 4 provides the metal-organic framework of any of Embodiments 2-3, wherein each (metal ion)$_6$ cluster is bound to 12, 8, or 4 tetratopic organic ligands.

Embodiment 5 provides the metal-organic framework of any of Embodiments 1-4, wherein the framework has a ftw topology.

Embodiment 6 provides the metal-organic framework of any of Embodiments 1-5, wherein the framework crystallizes in a trigonal crystal system.

Embodiment 7 provides the metal-organic framework of any of Embodiments 1-6, wherein the framework crystallizes in a R-3c space group.

Embodiment 8 provides the metal-organic framework of any of Embodiments 1-7, wherein the framework has unit cell dimensions a=18.0682(7) Å, c=45.3244(2) Å.

Embodiment 9 provides the metal-organic framework of any of Embodiments 1-8, wherein the framework has a unit volume of about 12814(1)Å$^3$.

Embodiment 10 provides the metal-organic framework of any of Embodiments 1-9, wherein the framework has a unit formula of Y$_6$(OH)$_8$(abtc)$_3$(H$_2$O)$_6$(DMA)$_2$, wherein DMA is dimethylammonium.

Embodiment 11 provides the metal-organic framework of any of Embodiments 1-10, wherein the framework has a surface area from about 300 m$^2$/g to about 500 m$^2$/g.

Embodiment 12 provides the metal-organic framework of any of Embodiments 1-11, wherein the framework has a micropore volume from about 0.10 cm$^2$/g to about 0.25 cm$^2$/g.

Embodiment 13 provides the metal-organic framework of any of Embodiments 1-12, wherein the framework has a pore or window size of about 4 Å to about 7 Å.

Embodiment 14 provides the metal-organic framework of any of Embodiments 1-13, wherein the framework is thermally stable up to about 400° C.

Embodiment 15 provides the metal-organic framework of any of Embodiments 1-14, wherein the framework has an X-ray powder diffraction spectrum comprising 2θ values (in degrees) of about 6.86, 9.63, 9.78, 11.40, 11.71, 11.96, 13.74, and 15.10.

Embodiment 16 provides the metal-organic framework of any of Embodiments 1-15, wherein the framework is capable of reversibly adsorbing from about 1 mmol/g to about 2 mmol/g of propylene (propylene/MOF).

Embodiment 17 provides a method of at least partially separating a first aliphatic hydrocarbon compound from at least one distinct aliphatic hydrocarbon compound, the method comprising contacting the first aliphatic hydrocarbon compound and the at least one distinct aliphatic hydrocarbon compound with a metal-organic framework of any of Embodiments 1-16, whereby the first aliphatic hydrocarbon compound and the at least one distinct aliphatic hydrocarbon compound are at least partially separated from one another.

Embodiment 18 provides the method of Embodiment 17, wherein the first aliphatic hydrocarbon compound and the at least one distinct aliphatic hydrocarbon compound are run through a column that is at least partially packed with the metal-organic framework.

Embodiment 19 provides the method of any of Embodiments 17-18, wherein the first aliphatic hydrocarbon compound is propylene and the at least one distinct aliphatic hydrocarbon compound is propane.

Embodiment 20 provides the method of any of Embodiments 17-19, wherein the metal-organic framework preferentially adsorbs propylene over propane.

Embodiment 21 provides the method of any of Embodiments 17-20, wherein the metal-organic framework preferentially adsorbs the first aliphatic hydrocarbon over the at least one distinct hydrocarbon compound.

Embodiment 22 provides the method of any of Embodiments 17-21, wherein the first aliphatic hydrocarbon compound and the at least one distinct aliphatic hydrocarbon compound are in gaseous form.

The disclosures of each and every patent, patent application, and publication cited herein are hereby incorporated herein by reference in their entirety. While this invention has been disclosed with reference to specific embodiments, it is apparent that other embodiments and variations of this invention can be devised by others skilled in the art without departing from the true spirit and scope of the invention. The appended claims are intended to be construed to include all such embodiments and equivalent variations

What is claimed is:

1. A metal-organic framework comprising a metal (M) ion and a tetratopic organic ligand selected from the group consisting of:

(a) the metal ion is Y$^{3+}$(M$^{3+}$), and the tetratopic organic ligand is

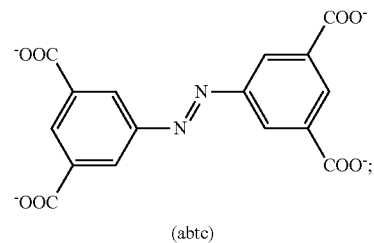

(abtc)

(b) the metal ion is-selected from the group consisting of Y$^{3+}$(M$^{3+}$), Zr$^{4+}$(M$^{4+}$), and Hf$^{4+}$(M$^{4+}$), and the tetratopic organic ligand is

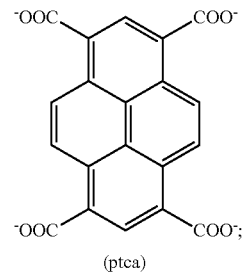

(ptca);

and (c) the metal ion is selected from the group consisting of Y$^{3+}$(M$^{3+}$), Zr$^{4+}$(M$^{4+}$), and Hf$^{4+}$(M$^{4+}$), and the tetratopic organic ligand is

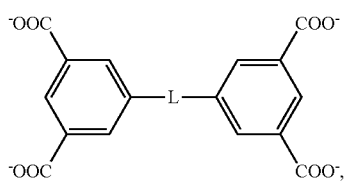

wherein L is selected from the group consisting of a bond, optionally substituted C$_1$-C$_6$ alkylene, optionally substituted C$_2$-C$_6$ alkenylene, optionally substituted C$_2$-C$_6$ alkynylene,

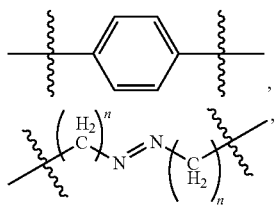

O, S, SO$_2$, NH and NCH$_3$, and wherein each instance of n is independently 1, 2, or 3.

2. The metal-organic framework of claim 1, wherein the metal ion is in the form of a (metal ion)$_6$ cluster.

3. The metal-organic framework of claim 2, wherein the (metal ion)$_6$ cluster comprises at least one selected from the group consisting of a μ$_3$-OH bridging ligand and a μ$_3$-O bridging ligand.

4. The metal-organic framework of claim 2, wherein the (metal ion)$_6$ cluster is bound to 12, 8, or 4 tetratopic organic ligands.

5. The metal-organic framework of claim 1, wherein the framework has a ftw topology.

6. The metal-organic framework of claim 1, wherein the framework crystallizes in a trigonal crystal system.

7. The metal-organic framework of claim 1, wherein the framework crystallizes in a R-3c space group.

8. The metal-organic framework of claim 7, wherein the framework has at least one of:

(a) unit cell dimensions a=18.0682(7) Å, c=45.3244(2) Å; and (b) a unit volume of about 12814(1)Å$^3$.

9. The metal-organic framework of claim 1, wherein the framework has a unit formula of Y$_6$(OH)$_8$(abtc)$_3$(H$_2$O)$_6$(DMA)$_2$, wherein DMA is dimethylammonium.

10. The metal-organic framework of claim 1, wherein the framework has at least one of:

(a) a surface area from about 300 m$^2$/g to about 500 m$^2$/g;

(b) a micropore volume from about 0.10 cm$^2$/g to about 0.25 cm$^2$/g; and (c) a pore or window size of about 4 Å to about 7 Å.

11. The metal-organic framework of claim 1, wherein the framework is thermally stable up to a temperature of about 400° C.

12. The metal-organic framework of claim 1, wherein the framework has an X-ray powder diffraction spectrum comprising 2θ values (in degrees) of about 6.86, 9.63, 9.78, 11.40, 11.71, 11.96, 13.74, and 15.10.

13. The metal-organic framework of claim 1, wherein the framework is capable of reversibly adsorbing from about 1 mmol/g to about 2 mmol/g of propylene (mmol propylene/g MOF).

14. A method of at least partially separating a first aliphatic hydrocarbon compound from at least one distinct aliphatic hydrocarbon compound, the method comprising contacting the first aliphatic hydrocarbon compound and the at least one distinct aliphatic hydrocarbon compound with the metal-organic framework of claim 1, whereby the first aliphatic hydrocarbon compound and the at least one distinct aliphatic hydrocarbon compound are at least partially separated from one another.

15. The method of claim 14, wherein the first aliphatic hydrocarbon compound and the at least one distinct aliphatic hydrocarbon compound are run through a column that is at least partially packed with the metal-organic framework.

16. The method of claim 14, wherein the first aliphatic hydrocarbon compound is propylene and the at least one distinct aliphatic hydrocarbon compound is propane.

17. The method of claim 16, wherein the metal-organic framework preferentially adsorbs propylene over propane.

18. The method of claim 14, wherein the metal-organic framework preferentially adsorbs the first aliphatic hydrocarbon over the at least one distinct hydrocarbon compound.

19. The method of claim 14, wherein the first aliphatic hydrocarbon compound and the at least one distinct aliphatic hydrocarbon compound are in gaseous form.

20. The metal-organic framework of claim 1, wherein in (c) L is 1,2-ethylene and the metal ion is Y$^{3+}$(M$^{3+}$).

* * * * *